(12) United States Patent
Sakata et al.

(10) Patent No.: US 6,244,870 B1
(45) Date of Patent: Jun. 12, 2001

(54) ABUTMENT TOOTH MODEL AND METHOD OF MANUFACTURING A PROSTHETIC RESTORATION TO BE FORMED ON THE ABUTMENT TOOTH MODEL

(75) Inventors: Masaaki Sakata, Suwa; Kenichi Shimodaira, Nagano-ken; Michio Ito, Shiojiri, all of (JP)

(73) Assignees: Injex Corporation; Matsumoto Dental College, both of Nagano-ken (JP)

( * ) Notice: Subject to any disclaimer, the term of this patent is extended or adjusted under 35 U.S.C. 154(b) by 0 days.

(21) Appl. No.: 09/055,606

(22) Filed: Apr. 6, 1998

(30) Foreign Application Priority Data

Apr. 4, 1997 (JP) .................................. 9-086557

(51) Int. Cl.$^7$ .................................. A61K 6/00
(52) U.S. Cl. .................. 433/213; 433/223; 106/38.22
(58) Field of Search .................. 433/206, 207, 433/213, 223; 106/38.22

(56) References Cited

U.S. PATENT DOCUMENTS

| | | | |
|---|---|---|---|
| 4,415,673 | * 11/1983 | Feagin | 501/102 |
| 4,661,071 | * 4/1987 | Bell et al. | 433/223 |
| 4,703,806 | * 11/1987 | Lassow et al. | 106/38.3 |
| 4,740,246 | * 4/1988 | Feagin | 106/38.22 |
| 5,464,797 | * 11/1995 | Yasderi et al. | 106/38.2 |
| 5,500,041 | * 3/1996 | Debuigne et al. | 106/38.22 |
| 5,535,811 | * 7/1996 | Feagin | 106/38.22 |
| 5,766,329 | * 6/1998 | LaSalle et al. | 106/38.9 |
| 5,911,102 | * 6/1999 | Takahashi et al. | 419/38 |

FOREIGN PATENT DOCUMENTS 7-179960 * 7/1995 (JP) .

OTHER PUBLICATIONS

Y. Oda, "Method of Making Dental Prostheses by Means of Powder Alloy Sintering Method", *Quintessence of Dental Technology*, vol. 11, 1986.

Yutaka Oda, "Method of Manufacturing Prosthetics by Powder Alloy Sintering Method", *Quintessence of Dental Technology*, vol. 11, No. 9, 1986.

Yutaka Oda et al., "A Study on the Method of Preparing Dental Prosthetics by Sintered Titanium Alloys—A Influence of Addition of Aluminum Powder", *Journal of the Japanese Society for Dental Materials and Devices*, vol. 4, No. 5, 1985, pp. 491–495.

Yutaka Oda et al., "A Study of the Method of Making Dental Prosthetic Appliances by Sintered Titanium Alloys: Effect of Copper Powder Content on Properties of Sintered Titanium Alloy", *The Bulletin of Tokyo Dental College*, vol. 31, No. 2, 1990, pp. 47–52.

Yutaka Oda, "Studies on the Method of Making Dental Restorations by Powder Metallurgy", *Journal of the Japanese Association for Dental Science*, vol. 10, 1991, pp. 129–134.

* cited by examiner

*Primary Examiner*—Ralph A. Lewis
(74) *Attorney, Agent, or Firm*—Bell, Boyd & Lloyd LLC

(57) ABSTRACT

An abutment tooth model which can improve a mold releasable property of the prosthetic restoration (releasability from an abutment tooth model or a mold) and a method of manufacturing such a prosthetic restoration are provided The abutment tooth model is formed of a base material such as an ultra-hard plaster ($CaSO_4.2H_2O$), and at least one oxide selected from the group comprising Zr, Y and Ca. The abutment tooth model is formed so as to be slightly larger than the abutment tooth to the extent of the degree of shrinkage of the prosthetic restoration (green body) by taking the curing expansion upon molding and the thermal expansion upon sintering into account The abutment tooth is formed using a compound in which Ti powder or Tn alloy powder is contained as its main component, and the compound is built up onto the abutment tooth model 5 so as to have a desired shape, and thus obtained green body is subjected to a debinding treatment. Then, the green body is sintered together with the green body to obtain a prosthetic restoration composed of the metal sintered body

3 Claims, 9 Drawing Sheets

ABUTMENT TOOTH MODEL AND METHOD OF MANUFACTURING A PROSTHETIC RESTORATION TO BE FORMED ON THE ABUTMENT TOOTH MODEL

BACKGROUND OF THE INVENTION

1. Field of the Invention

This invention relates to an abutment tooth model and a method of manufacturing a prosthetic restoration to be formed on the abutment tooth model.

2. Description of the Prior Art

There are known prosthetic restorations. A prosthetic restoration is used by being attached to an abutment tooth which has been formed by giinding down a living tooth in the oral cavity. The prosthetic restoration is used by being bonded to and fixed on the abutment tooth with a dental cement.

Both (1) metals such as gold, silver and stainless steel and (2) ceramics such as zirconia, alumina and sapphire have been so far used as structural materials for such prosthetic restorations.

However, prosthetic restorations made of ceramic materials have a disadvantage in that they have lower toughness and therefore are liable to be damaged.

Furthermore, prosthetic restorations made of noble metals such as gold and silver are very expensive. Moreover, prosthetic restorations made of stainless steel have poor biocompatibility, so that they may have an adverse effect on the body such as the onset of metal allergies or the risk of carcinogenic actions due to the elusion of Ni and Cr in particular.

In view of the problems as described above, prosthetic restorations made of Ti (titanium) have been developed in recent years. Ti is light and very strong and has excellent corrosion resistance, and it does not give rise to adverse effects due to eluting materials as described above.

The prosthetic restorations made of Ti are manufactured as follows.

Firsts an abutment tooth model corresponding to the abutment tooth which has been prepared in the oral cavity is made from an ultra-hard plaster. Next, a compound containing Ti powder is built up onto the abutment tooth model to form a green body for a prosthetic restoration, and then the green body is subjected to a binder removal treatment. Thereafter, the green body is sintered together with the abutment tooth model. In this way, the prosthetic restoration comprised of a metal sintered body is obtained.

However, in the conventional manufacturing method for the prosthetic restorations, there is a disadvantage that the obtained prosthetic restoration is fragile and its mechanical strength is low, because Ti contained in the green body is reacted with the ultra-hard plaster during sinteling process so that an oxygen content at a portion of the prosthetic restoration to be in contact with the abutment tooth model increases.

Further, the prosthetic restoration is likely to be bonded to the abutment tooth model when being sintered due to the reaction between the Ti and the ultra- hard plaster As a result, there is a problem in that it becomes difficult to release the sintered prosthetic restoration from the abutment tooth model. Further, there is also a problem in that a reaction product is peeled off from the abutment tooth model and then it is attached to the prosthetic restoration, when the sintered prosthetic restoration is released from the abutment tooth model.

The attached reaction product causes changes in the property of the prosthetic restorations. Further, the reaction product is by nature unnecessary. Therefore, the reaction product is required to be removed. However, the removal operation of the reaction product is quite troublesome and the remainder thereof lowers the quality of the prosthetic restoration.

SUMMARY OF THE INVENTION

Accordingly, it is an object of the present invention to provide an abutment tooth model which can improve a mold releasable property of the prosthetic restoration (releasability from an abutment tooth model or a mold) and a method of manufacturing such a prosthetic restoration.

In order to achieve the object, the present invention is directed to an abutment tooth model used for manufacturing a green body for a prosthetic restoration to be attached to an abutment tooth. The green body is formed of a composition containing di powder or Ti alloy powder as its main component, and the abutment tooth model is adapted to be sintered together with the green body. The abutment tooth model has a portion to be in contact with said green body, and at least said portion of the abutment tooth model is formed of a material containing at least one oxide selected from the group comprising Zr, Y and Ca.

According to the invention as described above, it is possible to prevent reaction from being caused between Ti or Ti alloy in the green body and the abutment tooth model or the mold during sintering process, thereby enabling to improve a mold release property and to manufacture a high quality prosthetic restoration easily since no reaction product which is unnecessary by nature is attached thereto. Further, it is possible to provide a prosthetic restoration having excellent biocompatibility and bioaffinity, is light in weight, and has adequate mechanical strength and hardness.

In the present invention, the abutment tooth model may be formed of a material containing at least one oxide selected from the group comprising Zr, Y and Ca.

Further; the abutment tooth model may be provided with a surface layer which constitutes said portion of said abutment tooth model, and said surface layer is formed of a material containing at least one oxide selected fiom the group comprising Zr, Y and Ca as its main component. In this case, it it preferred that said surface layer has a thickness corresponding to a shrinkage which would occur when the green body is sintered.

When such a surface layer is formed on the abutment tooth model or the mold, the surface layer functions as a reaction preventing layer upon sintering. Further, the surface layer also functions as a spacer for compensating the shrinkage of the green body, so that it is not necessary to provide a spacer additionally, thus leading to easiness in manufacturing process.

The present invention is also directed to a method of manufacturing a prosthetic restoration. The method comprises the steps of: preparing an abutment tooth model; building up a green body for a prosthetic restoration which is to be attached to an abutment tooth onto said abutment tooth model, in which the green body being formed of a composition containing Ti powder or Ti alloy powder as its main component, and sintering the green body together with the abutment tooth model to manufacture the prosthetic restoration from the sintered body, wherein said abutment tooth model having a portion to be in contact with said green body, and at least said portion of the abutment tooth model being formed of a material containing at least one oxide selected from the group comprising Zr, Y and Ca.

In this method, it is preferred that the abutment tooth model is formed of a material containing at least one oxide selected from the group comprising Zr, Y and Ca.

Further, it is also preferred that the abutment tooth model includes a surface layer which constitutes said portion of said abutment tooth model, and said surface layer is formed of a material containing at least one oxide selected from the group comprising Zr, Y and Ca as its main component. In this case, it is also preferred that the surface layer has a thickness corresponding to a shrinkage that is caused when the green body is sintered.

Another aspect of the present invention is directed to a method of manufacturing a prosthetic restoration. This method comprises the steps of: preparing an inner mold and an outer mold for defining a cavity between said inner and outer molds; injecting a composition containing Ti powder or Ti alloy powder as its main component into said cavity to obtain a green body for a prosthetic restoration; and sintering the green body together with the inner and outer molds to manufacture the prosthetic restoration from the sintered body, wherein said inner and/or outer molds include a portion to be in contact with the green body, and at least the portion of said molds is formed of a material containing at least one oxide selected from the group comprising Zr, Y and Ca.

In this method, it is preferred that both the inner and/or outer molds are formed of a material containing at least one oxide selected from the group comprising Zi; Y and Ca.

In this method, it is also preferred that said green body is obtained using a slip casting method. Alternatively, said green body can be obtained by injecting the composition into the cavity to fill it with the composition.

Furthermore, in this method, it is also preferred that at least the portion of said inner and outer molds which is to be in contact with the green body includes a surface layer, and said surface layer is formed of a material containing at least one oxide selected from the group comprising Zr, Y and Ca as its main component. In this case, it is also preferred that said surface layer has a thickness corresponding to a shrinkage that would occur when the green body is sintered.

In this method, said green body can be obtained using a slip casting method. a Alternatively, said green body can be obtained by injecting the composition into the cavity to fill it with the composition.

Other aspect of the present invention is directed to a method of manufacturing a prosthetic restoration. This method comprises the steps of: preparing a mold defining a cavity therein; injecting a composition containing Ti powder or Ti alloy powder as its main component into said cavity to obtain a green body for a prosthetic restoration; and sintering the green body together with the mold to manufacture the prosthetic restoration from the sintered body, wherein said mold has a portion which exposes to said cavity, and at least said portion of said mold is formed of a material containing at least one oxide selected from the group comprising Zr, Y and Ca.

In this method, said green body may be obtained using a slip casting method. Alternatively, said green body may be obtained by injecting the composition into the cavity to fill it with the composition.

Other objects, structures and results of the present invention will be apparent when the following description of the preferred embodiment is considered taking in conjunction with the attached drawings.

DETAILED DESCRIPTION OF THE PREFERRED EMBODIMENTS

Hereinbelow, an abutment tooth model and a method of manufacturing a prosthetic restoration to be formed onto the abutment tooth model according to the present invention will be described in detail with reference to the preferred embodiments shown in the attached drawings.

Figure 1:
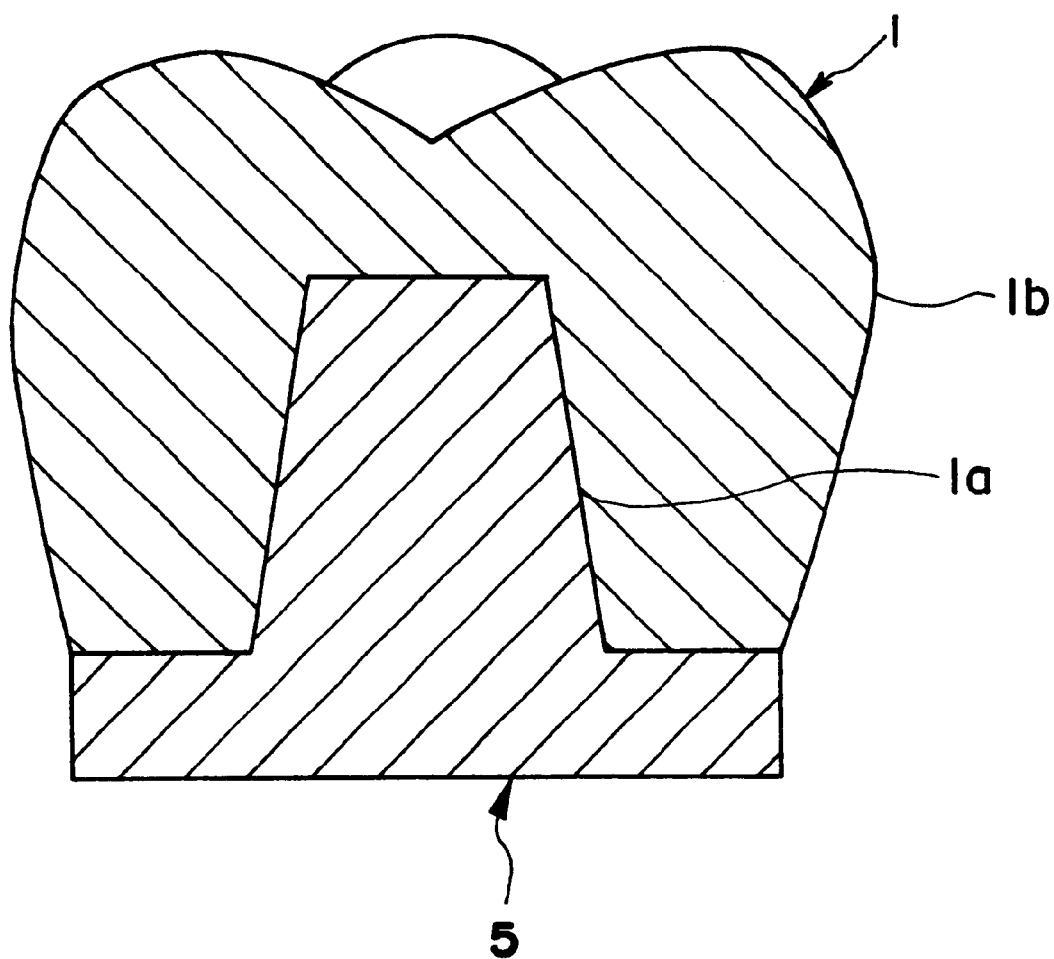
FIG. 1 is a cross sectional view which shows a first embodiment of an abutment tooth model according to the present invention.

FIG. 1 is a cross sectional view which shows a first embodiment of the abutment tooth model 5 according to the present invention. As shown in this drawing, the abutment tooth model 5 of the present invention is formed into a shape corresponding to the shape of an abutment tooth which has been in advance formed in the oral cavity and to which a prosthetic restoration (prosthesis) 1 is to be attached. The abutment tooth model 5 is used for manufacturing a green body, for the prosthetic restoration, and the green body is formed of a composition containing Ti powder or Ti alloy powder as its main component. Namely, the prosthetic restoration is formed onto the abutment tooth model 5.

The prosthetic restoration 1 is made of a metal material (a metal sintered body) such as those described below.

Namely, the composition of the metal material from which the prosthetic restoration 1 is formed (hereinafter, referred to simply as "metal material") contains Ti as its main component.

Ti is light and has high strength and appropriate hardness, and therefore Ti is not liable to deformation or damage, so that Ti has excellent durability and corrosion resistance. Further, Ti also has an advantage of inhibiting the onset of metal allergy and the like (it has excellent biocompatibility and bioaffinity) since there is very little elusion of the metal component. Moreover. Ti has less luster than stainless steel, so that it is aesthetically superior to stainless steel.

Further, it is preferred that the metal material contains a prescribed amount of M (where M is at least one element selected from the group comprising Si, Zr, Ca, P and In). In the case, M is present in the metal material in a form where the Ti and M have formed a solid solution for example.

The affinity of the prosthetic restoration 1 with respect to the abutment tooth and the gingival tissues, that is to say its biocompatibility (bioaffinity), is improved by including the M in the metal material. Further, bonding strength of the prosthetic restoration with respect to the abutment tooth is also improved. Namely, the prosthetic restoration 1 has an inner surface (which is the part to be in contact with the protruding part of the abutment tooth model 5) and a lower end surface, and the prosthetic restoration 1 is attached to the abutment tooth 5 through these surfaces using an adhesive (dental cement for example). In this connection, if the metal material contains the M therein, the bonding strength is improved, thereby preventing the prosthetic restoration from being fallen off from the abutment tooth 5. Further, in the case where a coating layer (not shown in the drawings) as described hereinbelow is formed on the outer surface of the prosthetic restoration 1, the adhesive property of said coating layer with respect to the prosthetic restoration is improved, thereby preventing peeling of or damage to the coating layer from being caused.

In the present invention, there is no particular limitation on the amount of M to be contained in the metal material, but about 0.01 to 3 wt % is preferable, 0.03 to 2.5 wt % is more preferable, and 0.05 to 1.5 wt % is most preferable.

If the amount of M included in the metal material is less than 0.01 wt %, the effects described above are not realized satisfactorily. On the other hand, if the amount exceeds 3 wt %, the strength and hardness of the metal material are lowered.

Furthermore, it is also preferred that the metal material contains a prescribed amount of Q (where Q is at least one element selected from the group comprising Al, Sn, V and Cu).

By including the Q in the metal material, the bonding strength of the prosthetic restoration 1 with respect to the abutment tooth and the adhesive property of a coating layer which is formed on the surface of the prosthetic restoration 1 can be further improved.

In the present invention, there is no particular limitation on the amount of Q to be contained in the metal material, but about 0.01 to 4 wt % is preferable, and 0.05 to 3 wt % is more preferable.

If the amount of Q in the metal material is less than 0.01 wt %, the improvement of the effects described above becomes insufficient. On the other hand, if the amount of Q in the metal material exceeds 4 wt %, the toughness of the metal material becomes lowered.

Furthermore, other elements, such as Fe, Cr, Pd, Co, Mo, Au and Ag for example, may be included either unavoidably or intentionally in the metal material. The addition of these elements contributes towards increasing the strength of the metal material. In this connection, it is preferred that these elements are present in the form of an alloy with Ti, an intermetallic compound or a metal oxide.

In the present invention, it is preferred that such a metal material has an appropriate porosity. Namely, it is preferable that a porosity of the metal material is about 0.1 to 5 vol %, and it is more preferable that a porosity of the metal material is about 0.3 to 4 vol %. If the porosity of the metal material is less than 0.1 vol %, the adhesive property of a coating layer with respect to the prosthetic restoration is lowered when such a coating layer is formed onto the prosthetic restoration, in particular, such a coating layer is formed of a ceramic material. On the other hand. if the porosity of the metal material exceeds 5 vol %, the strength and hardness of the metal material are lowered. In addition, since the pores tend to become coarser particles of food, for example, can be easily enter the pores, so that the propagation of bacteria is liable to occur.

In the present invention, there is no particular limitation on the average size (diameter) of the pores in the metal material, but it is preferable that a diameter of the pores lies within the range of from 2 to 100 μm, and it is more preferable that a diameter of the pores lies within the range of from 5 to 50 μm. With such a pore size, the strength and hardness of the metal material are maintained at a high level and the propagation of bacteria which is caused by the entry of food into cavities are suppressed.

Further, a coating layer (not shown in the drawing) may be formed on the surface of the prosthetic restoration 1.

There is no particular limitation to the purpose of formation of the coating layer. For example, it can be formed as a coloring layer. In this way, it becomes possible to form a prosthetic restoration having a color close to that of natural teeth, thereby improving the aesthetics of the prosthetic restoration. As for a preferred example of a structural material for the coating layer which is formed for this purpose, ceramic materials (Porcelain) can be mentioned.

No particular limitation is imposed upon the thickness of the coating layer; especially the thickness of the coating layer made of a porcelain, but, normally, it is preferable that its thickness lies within the range of from 0.1 to 2 mm, and it is more preferable that a thickness lies within the range of from 0.1 to 1 mm.

In this regard, it is to be noted that the purpose of formation of the coating layer is not limited to the formation of the coloring layer described above, and it may be formed for any purpose, for example as a protective layer a water excluding layer or a buffering layer or the like. Further, the structural material of the coating layer can be determined appropriately in accordance with the purpose for which such a coating layer is formed. For example, it may be formed from various synthetic resins besides the aforementioned porcelain. Examples of such synthetic resins include curable resins such as heat curable resins, light curable resins and those which are cured by reaction, and rigid resins are especially preferred.

Next, the abutment tooth model 5 according to this invention will be described.

Materials from which the abutment tooth model 5 shown in FIG. 1 is manufactured (hereinafter, referred to simply as "mold material") contain a base material and at least one oxide selected from the group comprising Zr, Y, and Ca Examples of the base material include ultra-hard plaster ($CaSO_4 \cdot 2H_2O$), aluminous cement and the like.

Further; it is preferred that the above-mentioned oxide of Zi; Y or Ca is formed into zirconia ($ZrO_2$), yttria ($Y_2O_3$) or calcia (CaO), respectively.

The mold release property of the prosthetic restoration 1 from the abutment tooth model 5 is improved by including at least one oxide selected from the group comprising Zr, Y, and Ca in the mold material. As a result, it is possible to prevent that Ti or Ti alloy included in the prosthetic restoration 1 (green body) is reacted with the abutment tooth model 5 during the sintering process (Process 5).

The amount of the oxide included in the mold material is preferably 40 wt % or more, more preferably about 40 to 95 wt %.

If the amount of the oxide contained in the mold material is less than 40 wt %, there is a case that the effects described above are not realized satisfactorily.

The abutment tooth model 5 is formed with dimensions slightly larger than the abutment tooth 5 in the oral cavity by taking the curing expansion upon molding and the thermal expansion upon sintering and the like into account. In more detail, the abutment tooth model 5 is formed so as to be larger than the abutment tooth in the oral cavity to the extent of the degree of shrinkage of the inner part 1a of the prosthetic restoration (green body) 1 that would occur during sintering process. Hereinafter, the degree of shrinkage is referred to as "inner part shrinkage".

Further, the mold material may contain other components such as Si, Mg or P or the like or its oxide.

Hereinbelow, a second embodiment of the abutment tooth model according to the present invention is described in details.

Figure 2:
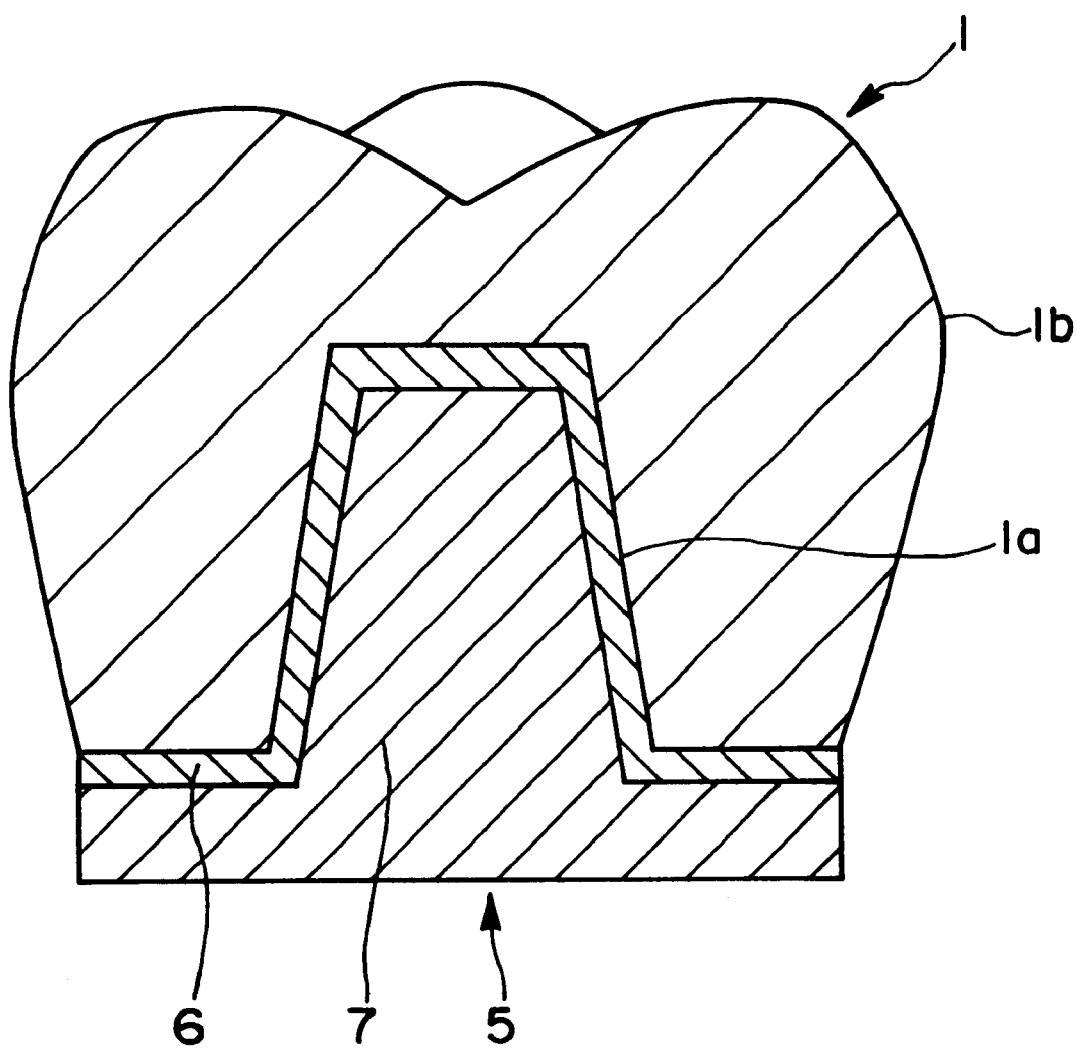
FIG. 2 is a cross sectional view which shows a second embodiment of an abutment tooth model according to the present invention.

FIG. 2 is a cross sectional view which shows the second embodiment of the abutment tooth model according to the present invention. The abutment tooth model 5 is provided with a surface layer 6 on the upper surface thereof (upper side in FIG. 2), that is a portion (region) of the abutment tooth model 5 which is adapted to be in contact with the prosthetic restoration (green body) 1.

The surface layer 6 is formed of a material containing at least one oxide selected from the group comprising Zr, Y and Ca as its main component.

By providing such a surface layer 6, the mold release property of the prosthetic restoration 1 from the abutment tooth model 5 is improved as described above.

In this case, it is preferred that the material of the surface layer 6 does not contain any material that is liable to react with Ti or Ti alloy, such as ultra-hard plaster or aluminous cement. If such a reactive material is contained in the material of the surface layer, it is preferred that the amount of the reactive material should be as little as possible. In this way, the mold release property of the prosthetic restorations from-the abutment tooth model 5 is further improved.

As for examples of the oxide of Zr, Y and Ca, zirconia ($ZrO_2$), yttria $Y_2O_3$) and calcia (CaO) can be mentioned, respectively.

Further, the amount of the oxide contained in the surface layer 6 is preferably equal to or more than 70wt %, and more preferably equal to or more than 90wt %, and most preferably equal to or more than 98wt %.

If the amount of the oxide contained in the mold material is too little, the effects described above are not realized satisfactorily.

There is no particular limitation on the composition of the inner part 7 of the abutment tooth model 5 shown in FIG. 2. For example, the inner part 7 can be formed of ultra-hard plaster, alumina cement or the like.

Further, the boundary between the inner part 7 and the surface layer 6 need not be distinct like that shown in the drawing, and the composition and the like may vary continuously in the vicinity of this boundary.

There is no particular limitation on the thickness of the surface layer 6. but, normally, the thickness of the surface layer 6 is preferably about 0.01 to 2mm, and more preferable about 0.1 to 1 mm.

If the thickness of the surface layer 6 is less than 0.01 mm, there is a case that the effects described above are not realized satisfactorily depending on the composition of the material from which the surface layer 6 is formed. On the other hand, if the thickness of the surface layer 6 exceeds 2 mm, a defect such as crack, chipping and the like is liable to occur.

Such a surface layer 6 serves to compensate (offset) the inner part shrinkage of the prosthetic restoration (green body) 1 during sintering process so that the inner part of the prosthetic restoration 1 can be fitted to an intended shape by adjusting its thickness (preferably such adjustment is made within the range described above).

In this invention, it is preferred that the thickness of the surface layer 6 is determined so as to correspond to the inner part shrinkage cased upon sintering the green body.

In this way, it is not necessary to use a spacer having a thickness corresponding to the inner part shrinkage upon sintering the green body. Therefore, the prosthetic restoration 1 can be easily manufactured without increasing the manufacturing process.

Hereinbelow, a third embodiment of the abutment tooth model according to the present invention will be described in details.

Figure 3:
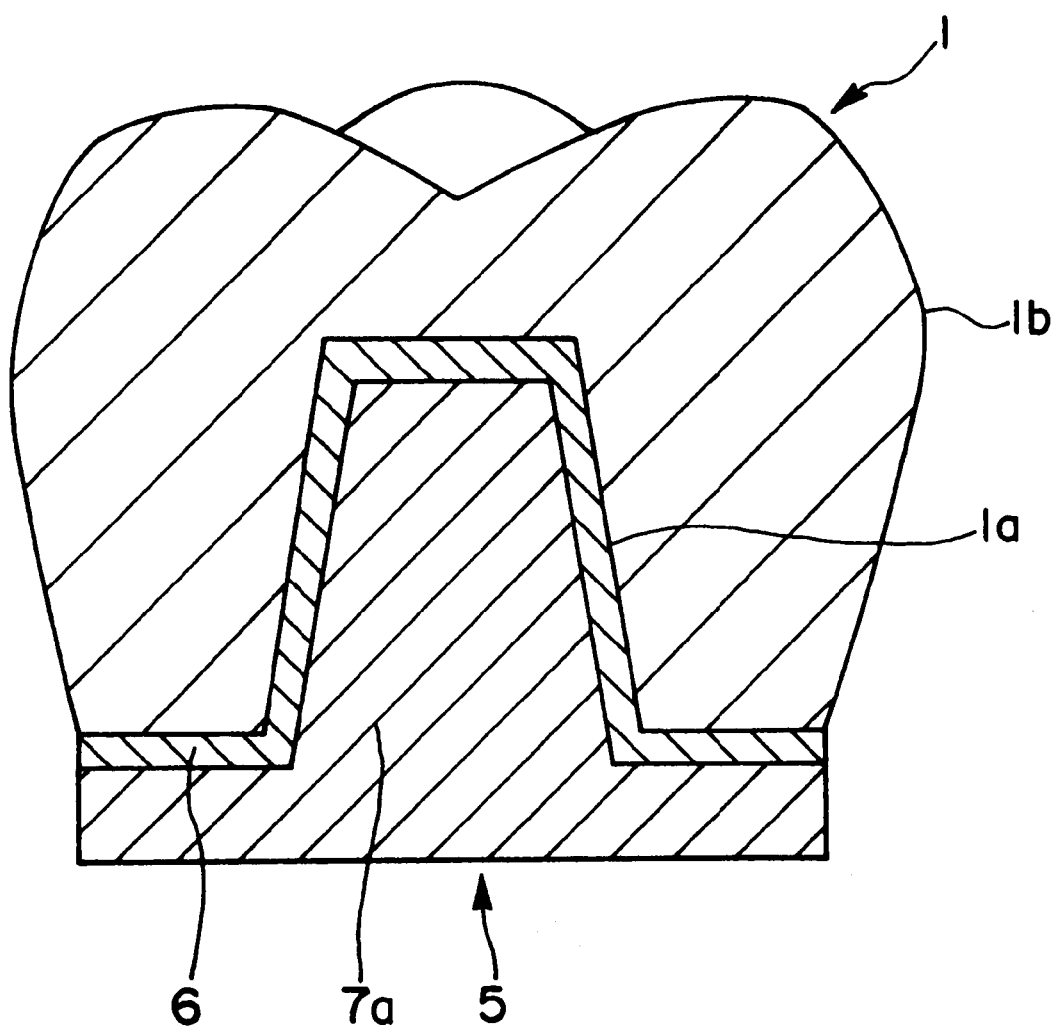
FIG. 3 is a cross sectional view which shows a third embodiment of an abutment tooth model according to the present invention.

FIG. 3 is a cross sectional view which shows the third embodiment of an abutment tooth model according to the present invention. The abutment tooth model 5 shown in this drawing has a surface layer 6 on an upper surface thereof (upper side in FIG. 3), that is at a portion adapted to be in contact with the prosthetic restoration (green body) 1. Since this surface layer 6 is the same as the surface layer 6 of the abutment tooth model shown in FIG. 2, the detailed description thereof is omitted.

The inner part 7a of the abutment tooth model 5 shown in FIG. 3 is formed from the same material as that of the mold for the abutment tooth model 5 shown in FIG. 1.

In this abutment tooth model 5, the mold release property of the prosthetic restoration 1 from the abutment tooth model 5 is also improved in the same manner as the previous embodiments.

Further, because an oxide of Zr, Y or Ca is contained in the inner part 7a, the adhesive property of the surface layer 6 with respect to inner part 7a is improved, thereby preventing peeling of the surface layer 6 or damage to the surface layer 6 from being caused.

Furthermore, since an oxide of Zr, Y or Ca is contained in the inner part 7a, it is possible to prevent reaction between Ti or Ti alloy contained in the prosthetic restoration (green body) 1 and the abutment tooth model 5 from being caused during sintering process, even if peeling off of the surface layer 6 or chipping or crack of the surface layer 6 should be caused.

Next, methods of manufacturing the prosthetic restoration according to the present invention will be described in details. In the present invention, the prosthetic restoration 1 is manufactured by powder metallurgy method in view of the factors such as the ease of production, the form and dimensional stability, and the ease of controlling the mechanical strength, hardness and porosity of the metal material. Hereinbelow, first, second and third embodiments of a method of manufacturing a prosthetic restoration are described.

<First Manufacturing Method>

(1) A composition for manufacturing an abutment tooth model is injected into an impression material taking the shape of an abutment tooth in the oral cavity of a patient. Then, the composition is cured to form an abutment tooth model 5 (any one of the abutment tooth models shown in FIGS. 1, 2 and 3).

As described above, this abutment tooth model 5 is formed so as to be larger than the abutment tooth to the extent of the degree of the inner part shrinkage of the prosthetic restoration (green body) 1 during sintering process, taking the curing expansion upon molding and thermal expansion upon sintering into account.

Then, as described above, when a surface layer 6 is formed onto the abutment tooth model 5, the shape of the abutment tooth model 5 can be fitted to the intended shape by adjusting the thickness of the surface layer 6. (that is, the abutment tooth model 5 including the surface layer 6 is formed so as to be slightly larger than the abutment tooth to an extent of the inner part shrinkage of the green body).

The surface layer 6 can be formed in accordance with the following method, for example. Namely, the surface layer 6 can be formed from a coating layer of an oxide which is obtained by applying a liquid type composition containing a prescribed amount of Zr, Y or Ca to the abutment tooth model 5 by a painting method or a dipping method, and then sintering the abutment tooth model 5 having the coating layer in an atmosphere containing oxygen.

Alternatively, it is possible to form a coating layer of an oxide by applying a liquid type composition containing a prescribed amount of zirconia ($ZrO_2$), yttria ($Y_2O_3$) or calcia (CaO) onto an abutment tooth model using the above described method and then sintering the abutment tooth model with the coating layer.

(2) On the other hand, a metal powder comprising Ti (or Ti alloy), a powder comprising M or M compound (especially the oxide thereof) as required, a powder comprising Q or Q compound (especially the oxide thereof) as necessary, and a binder (organic binder) are prepared, and then they are mixed and kneaded to produce a compound.

There is no particular limitation on the average particle size of the metal powder. But, in normal cases, it is preferable that its average particle size lies within the range of from 1 to 100 μm, and it is more preferable that its average particle size lies within the range of from 5 to 45 μm.

Further, there is also no particular limitation on the average particle size of the powder of M or M compound and the powder of Q or Q compound. But, in normal cases, it is preferable that their average particle size lies within the range of from 1 to 40 μm, and it is more preferable that their average particle size lies within the range of from 5 to 25 μm.

The compounding ratio of M or M compound and Q or Q compound with respect to the metal powder is determined such that the amount of M and Q of the metal material in the final composition lies within the ranges as described earlier Examples of the binder include various thermoplastic resins, for example polyolefins such as polyethylene, polypropylene and ethylene-vinyl acetate copolymer, acrylic resins such as polymethyl methacrylate and polybutyl methacrylate, styrene-based resins such as polystyrene, polyvinyl chloride, polyamide, polyester, polyether or copolymers containing at least one of such materials, various waxes, paraffins, higher fatty acids (for example stearic acid), higher alcohols, higher fatty acid esters, higher fatty acid amides and water soluble polymeric materials such as polyvinyl alcohol and methylcellulose and the like, which may be used alone or in combination of two or more.

The amount of such binder to be added is preferably less than 18 wt %, and more preferably 4 to 10 wt %. If too much binder is contained, the shrinkage that would occur upon sintering the green body which has been built up onto the abutment tooth model increases, thereby the dimensional accuracy is reduced, and the porosity also tends to increase. Furthermore, various additives, such as plasticizers, lubricants, antioxidants, debinding promoters and surfactants can be added to the compound, as necessary. As for examples of the plasticizers, phthalate esters (for example, DOP, DEP, DBP), adipic acid esters, trimelitic acid esters and sebacic acid esters can be mentioned.

(3) Next, using the compound obtained in the process (2) described above, the compound is built up manually onto the abutment tooth model 5 so as to be an intended shape. In this regard, it is preferred that the building up of the compound, that is manufacturing of a green body is performed so as to be slightly larger in shape and size than the intended shape (intended outer shape) by taking the sluinkage which would occur subsequently upon sintering into consideration.

Alternatively, when a coating layer is to be formed onto the prosthetic restoration 1, the above consideration is not necessary. Namely, in such a case, it is possible to compensate (offset) shrinkage of an outer part 1b of the prosthetic restoration (green body) 1 which would occur upon sintering (hereinafter, referred to as "outer part shrinkage") by adjusting the thickness of the coating layer. In this case, it is not necessary to adjust the amount of the compound to be built up by calculating shrinkage ratio or the like precisely beforehand, because it will be possible to obtain an abutment tooth model which is fittable to the intended shape easily only by adjusting the thickness of the coating layer when it will be formed later.

(4) Next, the built up compound (completed green bodv) is subjected to a binder removal treatment (debinding treatment).

The debinding treatment is carried out by a heat treatment in a non-oxidizing atmosphere, that is to say in a vacuum or under reduced pressure (for example at from $1 \times 10^{-1}$ to $1 \times 10^{-6}$ Torr), or in an inert gas such as argon gas, or under a reducing atmosphere.

In this case, the heat treatment is preferably carried out under conditions at a temperature of 50 to 650° C. for a period of 0.5 to 30 hours, and more preferably at a temperature of 100 to 550° C. for a period of 1 to 15 hours.

In this regard, instead of the debinding treatment described above, simple drying, such as natural drying or hot air drying under conditions of normal temperature and humidity for example, can be carried out.

(5) Then, the built up compound (green body) obtained in the aforementioned process (4) is sintered together with the abutment tooth model 5 to produce a prosthetic restoration 1 comprised of a metal sintered body. The sintering process can be performed just once, or it may be performed two or more times.

The sinterng process is preferably carried out under the condition at a temperature of 400 to 1450° C. for a period of 1 to 24 hours, more preferably at a temperature of 500 to 1400° C. for a period of 1.5 to 10 hours, and most preferably at a temperature of 850 to 1350° C. for a period of 2 to 7 hours.

In this case, the sintering process can be carried out in a non-oxidizing atmosphere, that is to say in a vacuum or under reduced pressure (for example at $1 \times 10^2$ to $1 \times 10^4$ Tbrr), or in an inert gas such as argon gas, or under a reducing atmosphere.

During the sintering process, the abutment tooth model 5 is broken due to shrinkage of the green body and the green body is shrunk to a prescribed size (intended shape).

In the present invention, the strength of the abutment tooth model 5 can be set higher in order to avoid the abutment tooth model 5 from being broken during the sintering process. In this case, it is preferred that the abutment tooth model 5 is formed so as to have substantially the same size as that of the abutment tooth.

As for examples of methods of enhancing the strength of abutment tooth model 5, a method in which the abutment tooth model is sintered at a high temperature or a method in which an alumina cement is used and the like can be mentioned.

(6) Furthermore, a coating layer is formed on the surface (e.g. outer surface) of the prosthetic restoration 1, as necessary.

In the case where a coating layer is to be formed with porcelain as described above, a slurry (compound) containing the material for the coating layer is first formed into a layer by painting or dipping method, for example, and then it is dried and sintered. In this case, a material for the coating layer may be formed as a layer on the outer surface of the built up compound (which has not yet been sintered) of the prosthetic restoration 1 and then both may be sintered at the same time.

Further, in the case where a coating layer is formed with a synthetic resin, a solution which contains an uncured resin is applied on the outer surface of the prosthetic restoration 1, for example, by painting or dipping method or the like to form a layer thereof, and then the resin is hardened (cured with heat, cured with light or cured by reaction, for example) to form the coating layer.

The method which is used to form the coating layer can be selected appropriately in accordance with its composition or the like, and it can be formed, for example, by means of thermal spraying or the like, in addition to the methods described above.

Furthermore, coating layers which have different compositions can be formed at different locations on the prosthetic restoration 1, or coating layers which have different compositions can be formed as laminates of two or more layers.

The formation of such coating layers is preferred since it makes up for the shrinkage of the metal material in the aforementioned process (1) and enables the intended shape to be realized.

(7) Next, the abutment tooth model 5 is released (removed) from the prosthetic restoration 1.

The prosthetic restoration 1 of this invention can be obtained by means of each of the processes described above.

According to this first method, since at least a portion of the abutment tooth model 5 which is to be in contact with the green body is formed from a material containing at least one oxide selected from the group comprising Zi; Y and Ca, unfavorable reaction will not occur between Ti or Ti alloy of the green body and the abutment tooth model 5 during the sintering process (5), thereby enabling to improve a mold release property of the prosthetic restoration 1 from the abutment tooth model 5 upon the mold releasing process (7).

Further, according to the method described above, it is possible to produce prosthetic restorations easily and with good dimensional accuracy even if the shape of each prosthetic restoration is complicated and intricate.

Furthermore, the prosthetic restoration 1 can be manufactured with good dimensional accuracy, and this reduces troublesome of correcting the prosthetic restoration 1 when it is to be attached to the abutment tooth.

Furthermore, for example, by adjusting the amount of the Al or Q to be added, composition of the metal material constituting the prosthetic restoration 1 can be determined as desired (and with delicacy).

Moreover, by adjusting the type of binder, the amount of the binder to be added, the conditions of the debinding treatment and the sintering conditions and the like, it is possible to desirably set various conditions of pore in the metal material constituting the prosthetic restoration 1. Examples of the conditions include the porosity and the pore diameter of the metal material.

On the basis of the facts outlined above, various conditions such as the physical properties of the metal material such as the mechanical strength and hardness, its chemical properties such as biocompatibility and corrosion resistance and its appearance can be controlled easily to the optimum conditions.

Hereinafter, the second method of manufacturing the prosthetic restoration will be described. In this connection, a detailed description of the manufacturing process which is the same as that of the first manufacturing methods is omitted, and only different points will be described.

<Second Manufacturing Method>

The second manufacturing method is carried out according to a slip casting method.

(1) First, a mold is manufactured.

Figure 4:
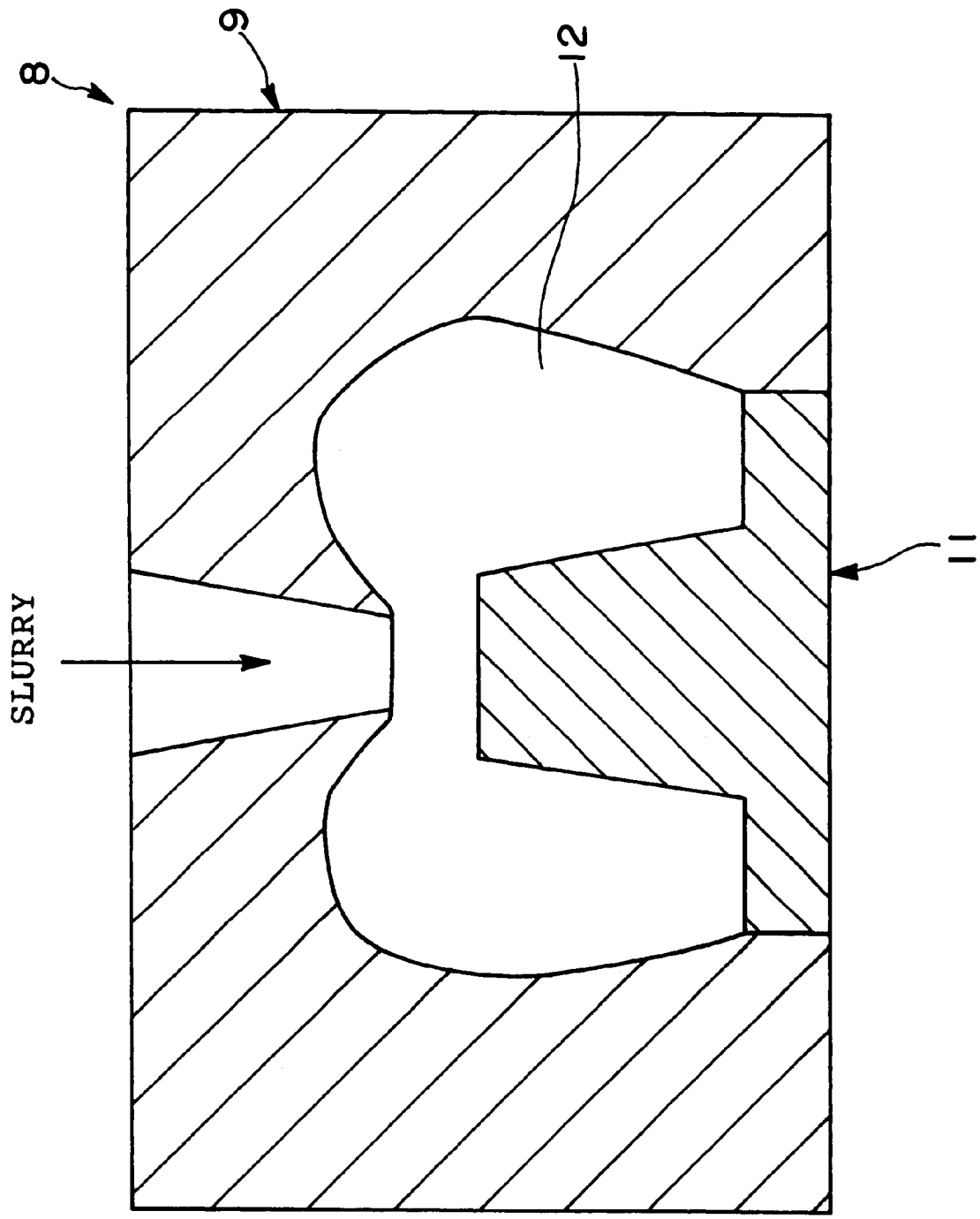
FIG. 4 is a cross sectional view which shows a first example of a structure of a mold which is to be used by the second manufacturing method of the present invention.
Figure 5:
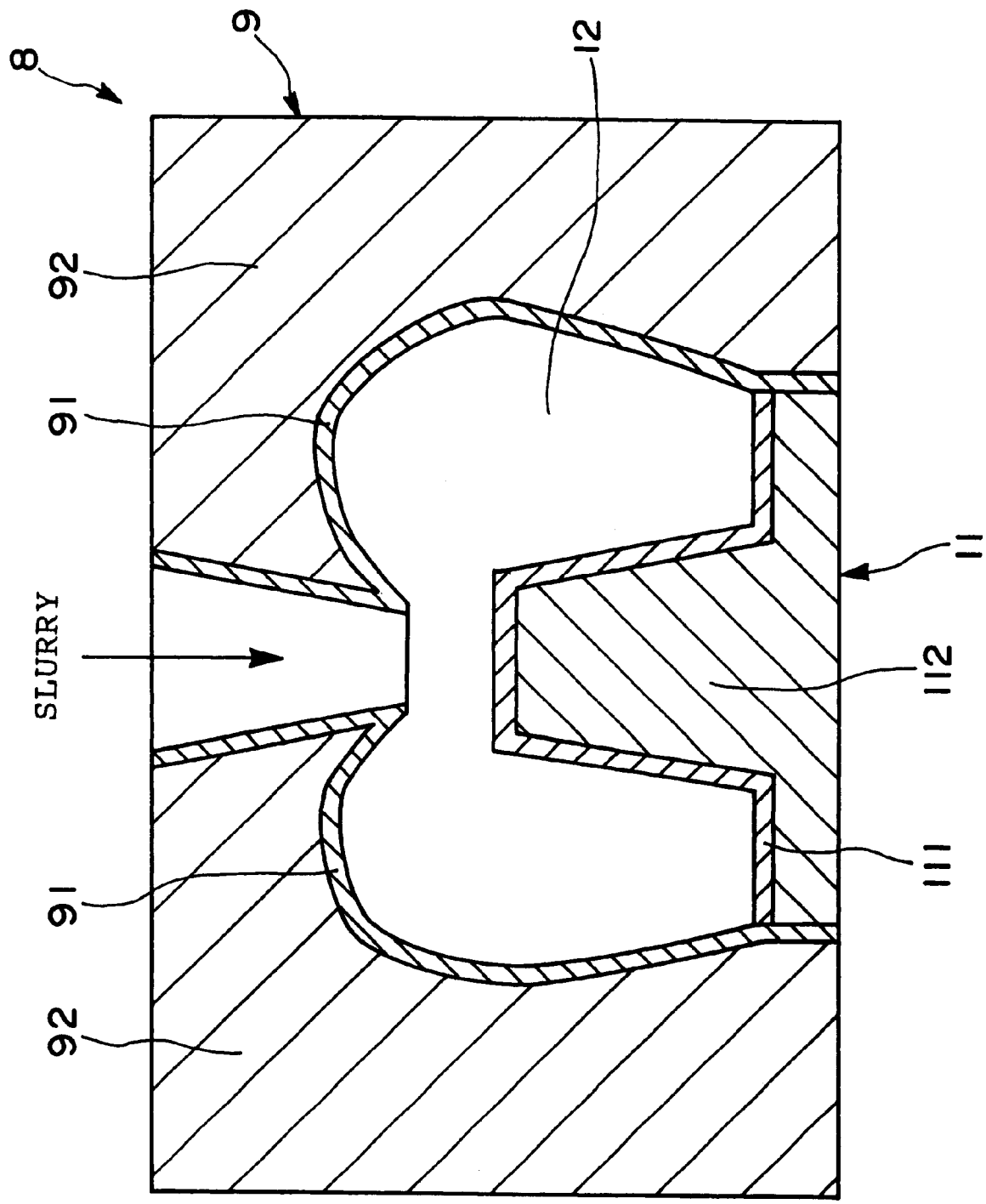
FIG. 5 is a cross sectional view which shows a second example of a structure of a mold which is to be used by the second manufacturing method of the present invention.
Figure 6:
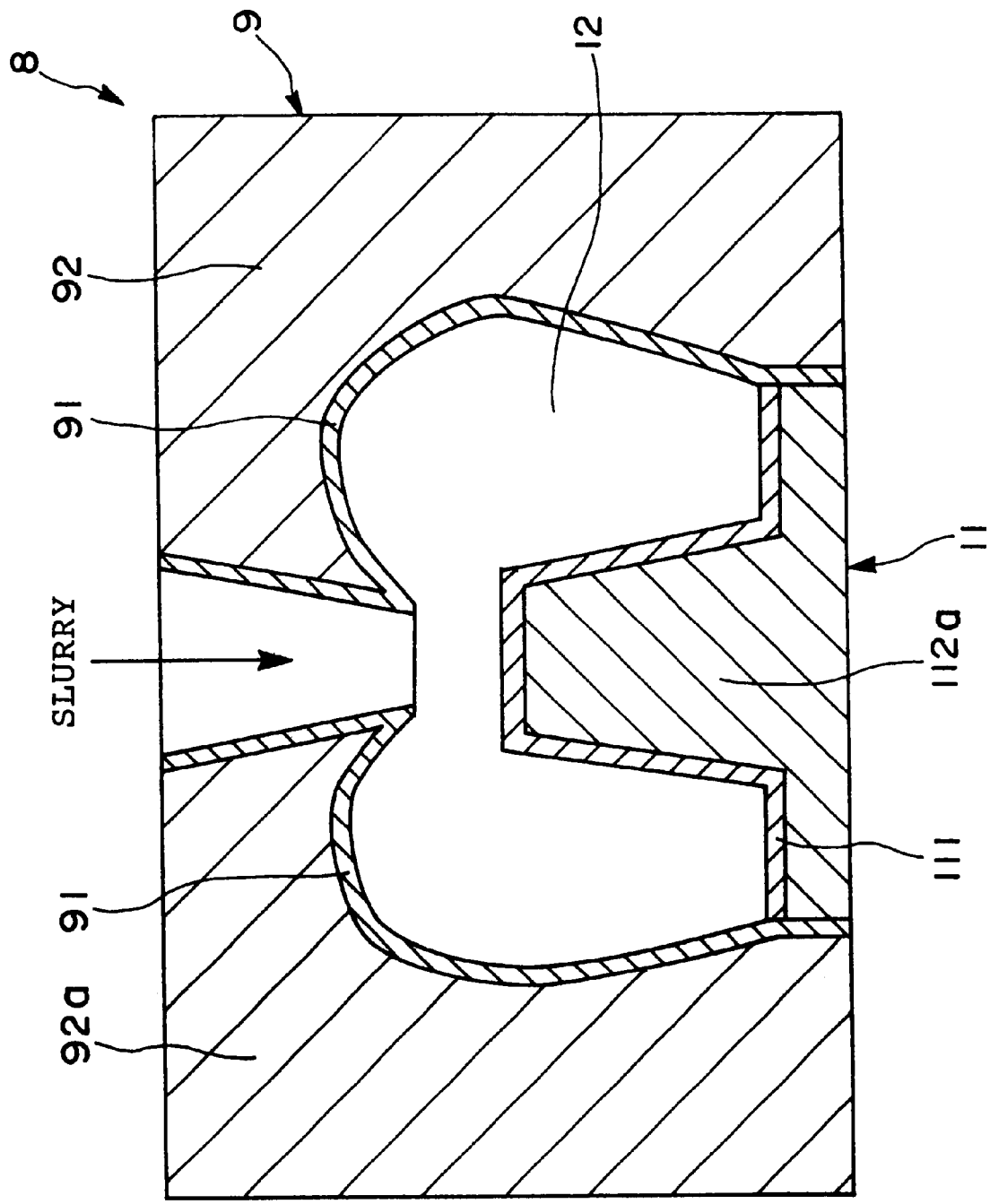
FIG. 6 is a cross sectional view which shows a third example of a structure of a mold which is to be used by the second manufacturing method of the present invention.

FIG. 4 is a cross-sectional view which shows a first example of a structure of a mold used in the second manufacturing method, FIG. 5 is a cross-sectional view which shows a second example of a structure of the mold used in the second manufacturing method, and FIG. 6 is a cross-sectional view which shows a third example of a structure of the mold used in the second manufacturing method. Hereinbelow, three types of molds shown in FIGS. 4 to 6 are described in details.

Each of the molds 8 shown in FIGS. 4 to 6 is composed of an outer mold 9 and an inner mold 11, respectively, and a cavity (molding space) 12 is defined between the outer mold 9 and the inner mold 11.

The inner mold 11 is manufactured in the same way as that of the abutment tooth model 5 described above. On the other hand, the outer mold 9 is obtained by building up a wax onto the inner mold 11, injecting a composition for producing the outer mold around the built up wax within a mold not shown in the drawing, and then curing the composition.

In the mold 8 shown in FIG. 4, the abutment tooth model 5 shown in FIG. 1 is used an inner mold 11 for the mold 8.

The material for forming the outer mold (hereinafter, referred to simply as "mold material") includes, as is the same with the abutment tooth model 5 shown in FIG. 1, a base material such as ultra-hard plaster, alumina cement or the like and at least one oxide selected from the group comprising Zr, Y and Ca.

In the same manner as the abutment tooth model 5 shown in FIG. 1, the outer mold 9 is formed so as to have a size slightly larger than an intended shape (intended outer shape) of the prosthetic restoration 1 taking a curing expansion upon molding and a thermal expansion upon sintering and the like into account. Namely, the outer mold 9 is formed so as to be larger than the intended shape of the prosthetic restoration 1 to the extent of the degree of the outer part shrinkage of the prosthetic restoration (green body) 1 during sintering process.

In this regard, since the details of the composition of the mold material are the same as those of the abutment tooth model 5 shown in FIG. 1, a detailed explanation thereof is omitted.

In the mold 8 shown in FIG. 5, the abutment tooth model 5 having the surface layer 6 shown in FIG. 2 described above is used as an inner mold 11 of the mold 8. Namely, the inner mold 11 has a surface layer 111 at a portion to be in contact with the prosthetic restoration (green body) 1. In this regard, it is to be noted that the composition of the inner part 112 of the inner mold 11 is not particularly limited as described above.

In the same manner as the abutment tooth model 5 shown in FIG. 2, the outer mold 9 includes a surface layer 91 at the inner surface thereof, that is at a portion to be in contact with the prosthetic restoration (green body) 1.

In the same way as the surface layer 6 of the abutment tooth model 5 shown in FIG. 2, the surface layer 91 is formed of a material containing at least one oxide selected from the group comprising Zr, Y, and Ca as its main component.

When the surface layer 91 is to be formed on the outer mold 9, the shape of the outer mold 9 is formed so as to be larger than an intended shape and then the thickness of the surface layer 91 is adjusted in the same way as was done in the abutment tooth model 5 shown in FIG. 2 so that the shape of the outer mold 9 is fitted to the intended shape. (that is, the outer mold 9 including the surface layer 91 is formed so as to be slightly larger than the abutment tooth to the extent of the outer part shrinkage of the green body).

For example, the formation of the surface layer 91 is canted out as follows.

First, the inner mold 11 is removed from the outer mold 9. Then, a prescribed amount of a liquid type composition containing Zr, Y or Ca is applied onto an inner surface of the outer mold 9 using a dipping or painting method, and the outer mold 9 with the applied composition is then sintered in an atmosphere containing oxygen to form a coating layer of an oxide. After the surface layer 91 is formed onto the outer mold 9 in this way, the outer mold 9 is fitted to the inner mold 11.

Alternatively, it is possible to form the coating layer of an oxide by applying a liquid type composition containing a prescribed amount of zirconia ($ZrO_2$), yttria ($T_2O_3$) or calcia (CaO) onto inner surface of the outer mold 9 using the above described method and then sintering it together with the outer mold 9.

In this connection, it is to be noted that in the present invention, such a surface layer can be formed on both the outer mold 9 and the inner mold 11 at the same time under the condition that the inner mold 11 is fitted to the outer mold 9.

Since the composition of the surface layer 91 is the same as that of the surface layer 6 of the abutment tooth model 5 shown in FIG. 2, a detailed description thereof is omitted.

Further, likewise the inner part 7 of the abutment tooth model 5 shown in FIG. 2, the composition of the inner part 92 of the outer mold 9 is not limited to a particular composition.

In the mold 8 shown in FIG. 6, the abutment tooth model 5 having the surface layer 6 shown in FIG. 3 described above can be used as an inner mold 11 of the mold 8. Namely the inner mold 11 has a surface layer 111 at a portion to be in contact with the prosthetic restoration (green body) 1, and the composition of the inner part 112a of the inner mold 11 is formed of the same material as the mold material of the above described abutment tooth model shown in FIG. 1.

The outer mold 9 is the same as the outer mold 9 of the above described mold 8 shown in FIG. 5 except that the composition of its inner part 92a is changed into the same composition of the inner part 7a of the abutment tooth model 5 shown in FIG. 3.

In the foregoing, three types of the molds 8 are described, but in the present invention the inner molds 11 and the outer molds 9 of these molds 8 can be selectively combined as desired. Namely, three types of the inner molds 11 which are formed from three types of the abutment tooth models shown in FIG. 1 to FIG. 3 can be combined with three types of the outer molds 9 having the same structure in a freely selectable manner.

Further, the compositions of the inner and outer molds 11 and 9 may be the same as with each other or different from with each other In more concrete, the composition of the surface layer 111 of the inner mold 11 may be the same as the composition of the surface layer 91 of the outer mold 9 or they may be different from with each other. Further, the composition of the inner part 112 (or 112a) of the inner mold 11 may be the same as the composition of the inner part 92 (or 92a) of the outer mold 9 or they may be different from with each other If the composition of the inner mold 11 is the same as the composition of the outer mold 9, the same material can be used for manufacturing the mold 8, which is quite advantageous for manufacturing the mold 8.

(2) On the other hand, a metal powder comprising Ti (or Ti alloy), a powder comprising M or M compound (especially the oxide thereof as required, a powder comprising Q or Q compound (especially the oxide thereof) as required, dispersing medium and the like are prepared, and then they are mixed or kneaded to produce a slurry (compositions).

Since the average particle sizes of the metal powder, the powder of M or M compound, or the powder of Q or Q compound and the compounding ratio thereof are the same as those of first manufacturing method described above, the detailed description thereof is omitted.

Further, examples of such a dispersing medium include water or organic matter such as alcohol, acetone and metylethyl-ketone and the like can be mentioned. In these dispersing mediums, water soluble polymeric materials such as agar, polyvinyl alcohol, methylcellulose and the like, polyvinyl acetate resin or polyvinyl butyral may be mixed as a binder, which can be used alone or in combination of two or more.

The amount of such the dispersing medium to be added is preferably about 10 to 50 wt %, more preferably about 15 to 40 wt %.

If the amount of the dispersing medium is too much, then the rate of shrinkage that would occur upon sintering the green body is increased, thereby the dimensional accuracy is reduced, and the porosity also tends to increase. On the other hands, if the amount of the dispersing medium is too small, then the flow characteristic of the slurry becomes insufficient.

Further, various additives, such as plasticizers, lubricants, antioxidants, defatting promoters and surfactants and the like can be added to the slurry, as necessary.

No particular limitation is imposed upon the viscosity of the slurry, but the viscosity of the slurry is preferably about 500 to 50,000 cps, and more preferably about 1,000 to 20,000 cps.

(3) The slurry obtained in the above-described process (2) is injected into the cavity 12 in the mold 8. In this way, the dispersing medium in the slurry is absorbed by the mold 8, so that the slurry is cured to obtain a green body. In this case, a holding time is determined so as to be such an extent that the dispersing medium in the slurry is fully absorbed by the mold 8.

(4) Then, the green body that has been completed is subjected to a binder removal treatment (debinding treatment). In this connection, since the various conditions in the debinding treatment, such as heat treatment condition, atmosphere and the like are the same as those of the first manufacturing method described above, the detailed description thereof is omitted.

(5) Then, the green body obtained in the above-described process (4) is sintered together with the mold 8 to produce a prosthetic restoration 1 comprised of a metal sintered body. In this connection, since the various conditions in the sintering process, such as sintering condition, sintering atmosphere and the like are the same as those of the first manufacturing method described above, the detailed description thereof is omitted.

(6) Then, the outer mold 9 and the inner mold 11 are removed from the prosthetic restoration 1, respectively.

(7) Further, a coating layer is formed on the surface (e.g. the outer surface) of the prosthetic restoration 1, as necessary.

A prosthetic restoration 1 of this invention can be obtained by means of each of the processes described above.

According to the second method, since at least a portion of the mold 8 which is to be in contact with the green body is formed from a material containing at least one oxide selected from the group comprising Zr, Y and Ca, unfavorable reaction will not occur between Ti or Ti alloy of the green body and the mold 8 during the sintering process (5), thereby enabling to improve a mold release property of the prosthetic restoration 1 from the mold 8.

Further, there are no problems with casting defects or melt runs that has been seen with a conventional casting method, so that prosthetic restorations can be produced easily and in good yield. In particular, it becomes possible to manufacture prosthetic restorations having no defect such as a pinhole and decrease dispersion in the qualities thereof Further, since the dispersing medium in the slurry is absorbed by the mold 8 during manufacturing the green body, it is possible to hold the shrinkage of the green body upon sintering as lower as possible.

Furthermore, it is possible to produce prosthetic restorations easily and with good dimensional accuracy even if the shape of each mold is complicated and intricate.

Furthermore, since the prosthetic restoration 1 can be manufactured with good dimensional accuracy, this reduces troublesome of correcting the prosthetic restoration 1 when it is to be attached to the abutment tooth.

Furthermore, for example, by adjusting the amount of the M or Q to be added, the composition of the metal material constituting the prosthetic restoration 1 can be determined as desired (and with delicacy).

Moreover, by adjusting the type of dispersion medium, the amount of the dispersion medium to be added, the conditions of the debinding treatment and the sintering conditions and the like, it is possible to desirably set the conditions for pore such as the porosity and the pore diameter of the metal material constituting the prosthetic restoration 1.

On the basis of the facts outlined above, various conditions such as the physical properties of the metal material such as the mechanical strength and hardness, its chemical properties such as biocompatibility and corrosion resistance and its appearance can be controlled easily to the optimum conditions.

Hereinafter, the third method of manufacturing the prosthetic restoration will be described. In this connection, a detailed description of the manufacturing process which is common with that of the second manufacturing method is omitted, and only different points will be described.

<Third Manufacturing Method>

The third manufacturing method is carried out according to a metal injection molding (MIM).

Figure 7:
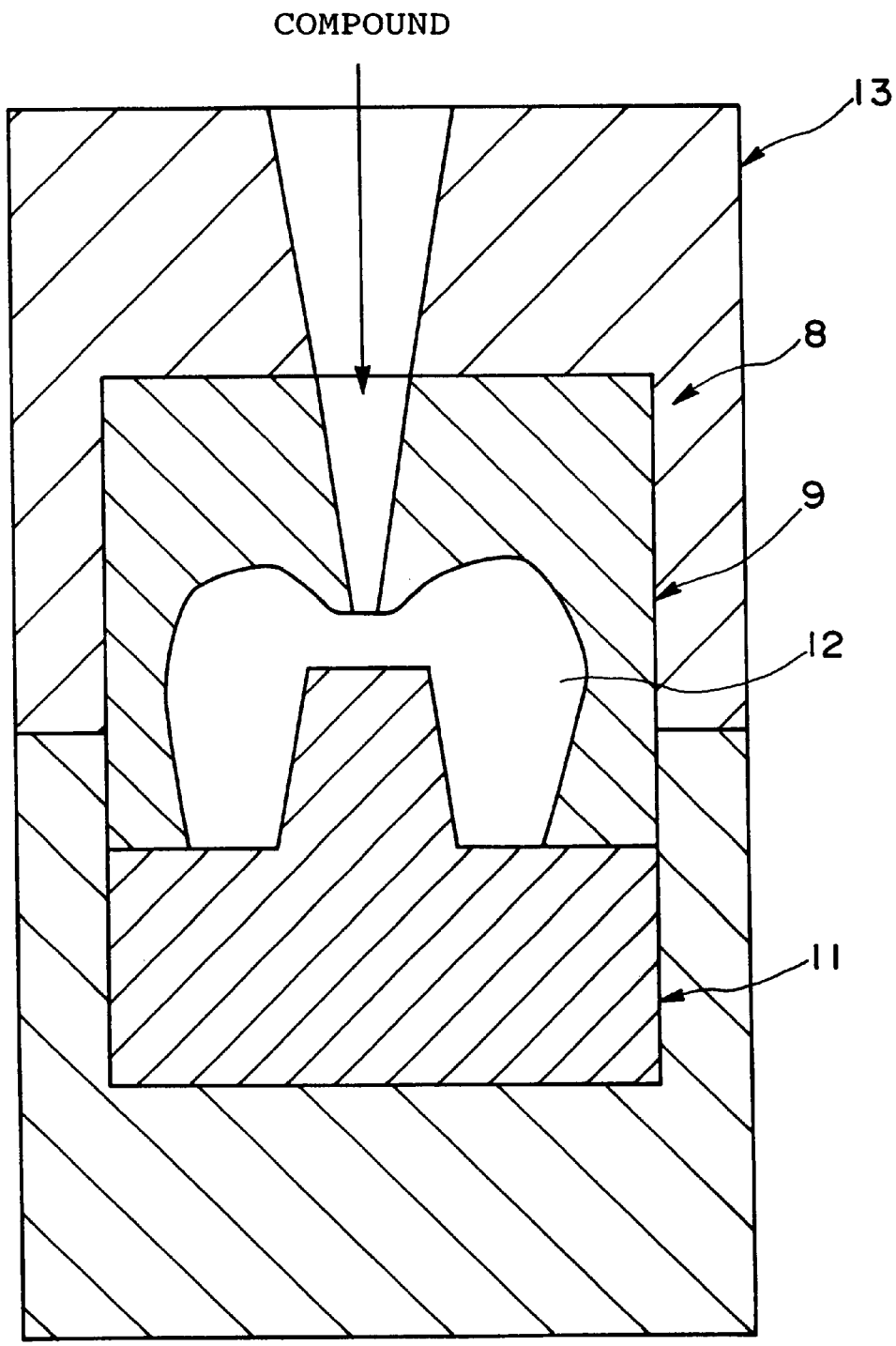
FIG. 7 is a cross sectional view which shows a first example of a die assembly and a mold which are to be used by the third manufacturing method of the present invention.
Figure 8:
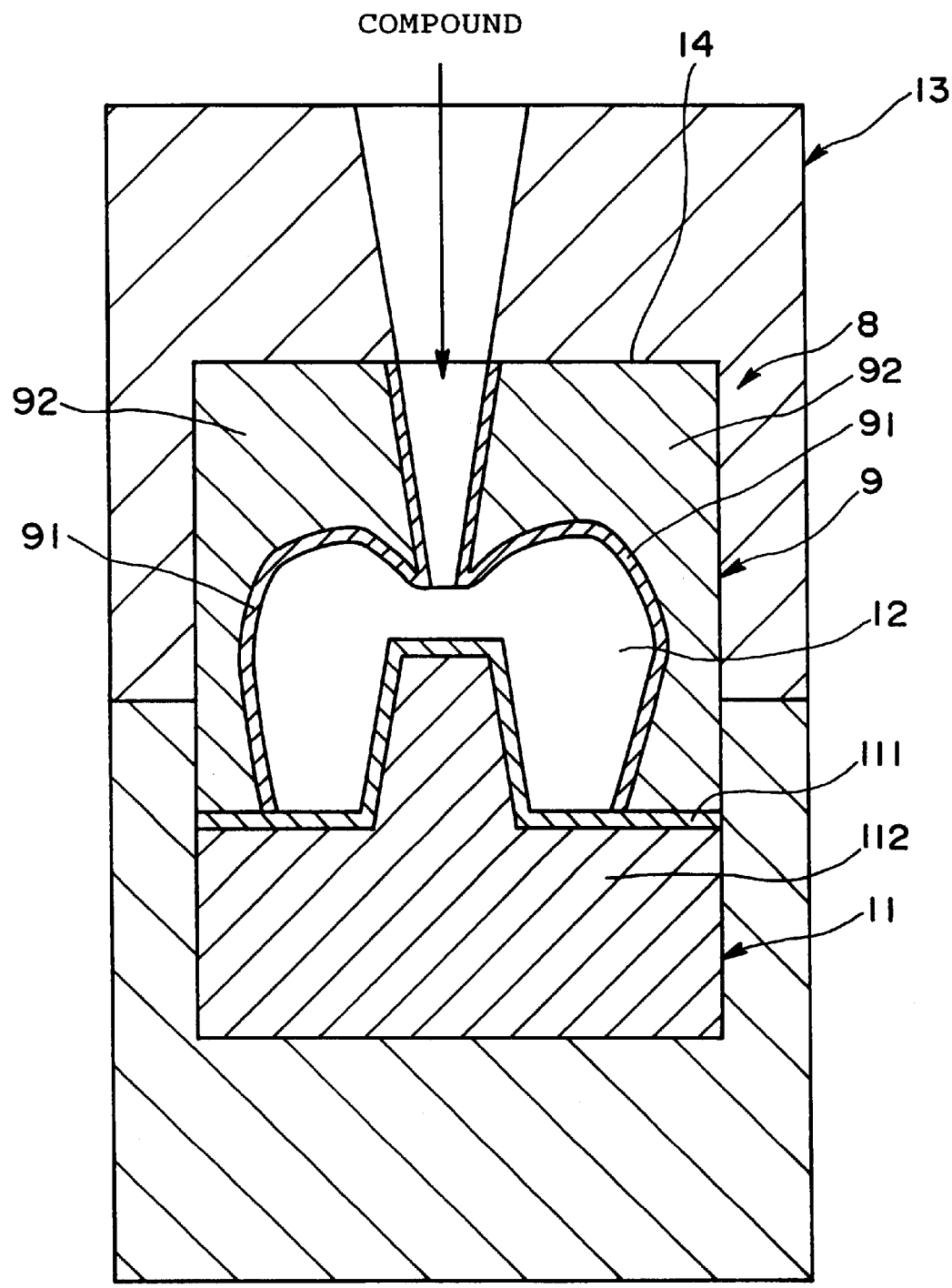
FIG. 8 is a cross sectional view which shows a second example of a die assembly and a mold which are to be used by the third manufacturing method of the present invention.
Figure 9:
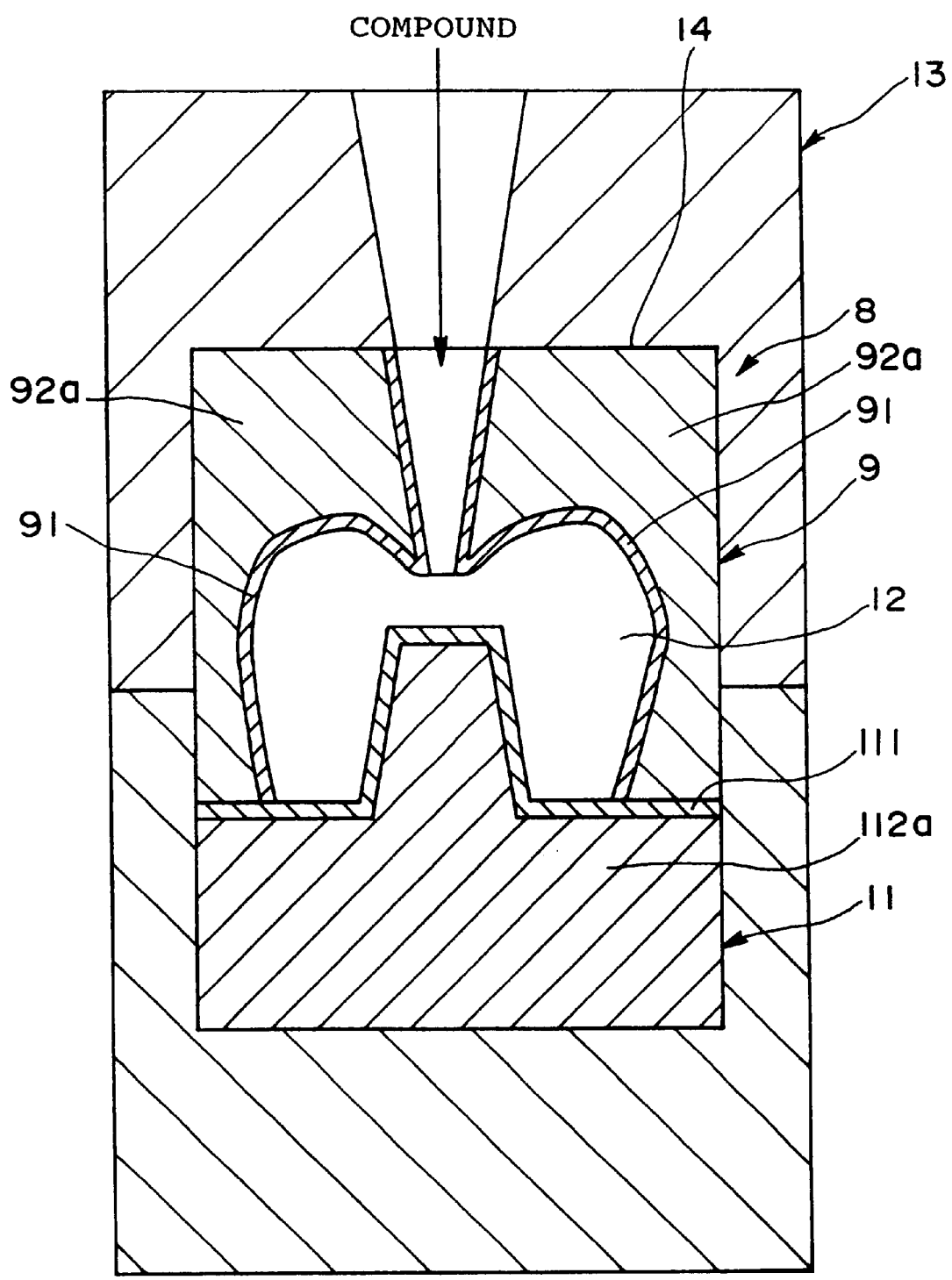
FIG. 9 is a cross sectional view which shows a third example of a die assembly and a mold which are to be used by the third manufacturing method of the present invention.

(1) FIG. 7 is a cross sectional view which shows a first example of a die assembly and a mold which are used by the third manufacturing method of the present invention, FIG. 8 is a cross sectional view which shows a second example of a die assembly and a mold which are used by the third manufacturing method of the present invention, and FIG. 9 is a cross sectional view which shows a third example of a die assembly and a mold which are used by the third manufacturing method of the present invention.

First, the molds 8 shown in FIGS. 7, 8 and 9 are manufactured. In this connection, since the molds 8 shown in FIGS. 7, 8 and 9 and methods of manufacturing thereof are the same as those of the molds 8 shown FIGS. 4, 5 and 6 described above, the detailed description thereof is omitted.

Then, each of thus manufactured molds 8 is mounted to a inner part 14 of a die assembly 13 of an injection molding machine not shown in the drawing. This die assembly 13 is used for holding the outer mold 9 and the inner mold 11 against injection pressure.

Further, in the same manner as the second manufacturing method described above, in the present invention the inner molds 11 and the outer molds 9 of these three types of molds 8 can be selectively combined as desired.

Further, the compositions of the inner and outer molds 11 and 9 may be the same as with each other or different from with each other. In more concrete, the composition of the surface layer 111 of the inner mold 11 may be the same as the composition of the surface layer 91 of the outer mold 9 or they may be different from with each other. Further, the composition of the inner part 112 (or 112a) of the inner mold 11 may be the same as the composition of the inner part 92 (or 92a) of the outer mold 9 or they may be different from with each other. If the composition of the inner mold 11 is the same as the composition of the outer mold 9, the same material can be used for manufacturing the mold 8, which is quite advantageous in manufacturing the mold 8.

(2) On the other hand, a metal powder comprising Ti (or Ti alloy), a powder comprising M or M compound (especially the oxide thereof as required, a powder comprising Q or Q compound (especially the oxide thereof as required, and a binder (organic binder) are prepared, and then they are mixed or kneaded to produce a compound.

The average particle size of the metal powder, the powder of M or M compound, or the powder of Q or Q compound and the compounding ratio thereof are the same as those of the second manufacturing method described above, the detailed description thereof is omitted.

Examples of the binder include various thermoplastic resins, for example polyolefins such as polyethylene, polypropylene and ethylene-vinyl acetate copolymer, acrylic resins such as poly-methyl methacrylate and polybutyl methacrylate, styrene-based resins such as polystyrene, polyvinyl chloride, polyamide, polyester, polyether or copolymers containing at least one of such materials, various waxes, paraffins, higher fatty acids (for example stealic acid), higher alcohols, higher fatty acid esters, higher fatty acid amides and water soluble polymeric materials such as polyvinyl alcohol and methylcellulose and the like, which may be used alone or in combination of two or more.

The amount of such binder to be added is preferably about 4 to 18 wt %. and more preferably 6 to 15 wt %.

If the amount of the binder to be added is too much, then the shrinkage that would occur upon sintering the green body is increased, thereby the dimensional accuracy is lowered, and the porosity also tends to increase. On the other hand, if the amount of the binder to be added is too little, the flow characteristic of the compound becomes insufficient.

Further, various additives, such as plasticizers, lubricants, antioxidants, defatting promotors and surfactants can be added to the compound, as necessary. As for examples of plasticizers, phthalate esters (for example, DOP, DEP, DBP), adipic acid esters, trimelitic acid esters and sebacic acid esters can be mentioned.

(3) Then, the compound obtained in the above described process (2) is injected into the cavity 12 of the mold to fill it with the compound (card-ing out an injection molding), thereby forming a green body.

In this case, as for examples of conditions for molding, the material temperature is preferably about 80 to 200° C., more preferably about 100 to 180° C. Further, the injection pressure is preferably about 50 to 600 kgf/cm$^2$, more preferably about 100 to 400 kgf/cm$^2$. Furthermore, the temperature at the mold is preferably 5 to 80° C., more preferably about 10 to 50° C.

(4) Then, the green body that has been completed is subjected to a binder removal treatment (debinding treatment). In this connection, since various conditions in the debinding treatment, such as heat treatment condition, atmosphere and the like are the same as those of the second manufacturing method described above, the detailed description thereof are omitted.

(5) Then, the green body obtained in the above-described process (4) is sintered together with the mold 8 to produce a prosthetic restoration 1 comprised of a metal sintered body. In this connection, since various conditions in the sintering process, such as sintering condition, sintering atmosphere and the like are the same as those of the second manufacturing method described above, the detailed description thereof are omitted.

(6) Then, the outer mold 9 and the inner mold 11 is released (removed) from the prosthetic restoration 1, respectively.

(7) Furthermore, a coating layer is formed on the surface (e.g. the outer surface) of the prosthetic restoration 1, as necessary.

A prosthetic restoration 1 of this invention can be obtained by means of each of the processes described above.

According to the third method, since at least a portion of the mold 8 which is to be in contact with the green body 8 is formed from a material containing at least one oxide selected from the group comprising Zr, Y and Ca, unfavorable reaction will not occur between Ti or Ti alloy of the green body and the mold 8 during the sintering process, thereby enabling to improve a mold release property of the prosthetic restoration 1 from the mold 8.

Further, there are no problems with casting defects or melt runs that has been seen with a conventional casting method, so that prosthetic restorations can be produced easily and in good yield. In particular, it becomes possible to manufacture prosthetic restorations having no defect such as a pinhole and decrease dispersion in the qualities thereof.

Further, according to the method described above, it is possible to produce prosthetic restorations easily and with good dimensional accuracy even if the shape of each prosthetic restoration is complicated and intricate.

Furthermore, since the prosthetic restoration 1 can be manufactured with good dimensional accuracy, this reduces troublesome of correcting the prosthetic restoration 1 when it is to be attached to the abutment tooth.

Moreover, the green body is formed by the injection molding, the compacting ratio of the metal powder, the powder of M or M compound, and the powder of Q or Q compound is improved in comparison with the second manufacturing method described above, so that the shrinkage rate of the green body upon sintering is relatively small, thus leading to good production yield.

Furthermore, by adjusting the amount of the M or Q to be added, the composition of the metal material constituting the prosthetic restoration 1 can be set as desired (and with delicacy).

Moreover, by adjusting the type of binder, the amount of the binder to be added, the conditions of the debinding treatment and the sintering conditions and the like, it is possible to desirably set the conditions for pore in the metal material constituting the prosthetic restoration 1. Examples of the conditions include the porosity and the pore size of the metal material.

On the basis of the facts outlined above, various conditions such as the physical properties of the metal material such as the mechanical strength and hardness, its chemical properties such as biocompatibility and corrosion resistance and its appearance can be controlled easily to the optimum conditions.

Hereinbelow, actual examples of an abutment tooth model and a method of manufacturing a prosthetic restoration to be formed on the abutment tooth according to the present invention are described in details.

EXAMPLES 1 to 7 and COMPARATIVE EXAMPLE 1

Prosthetic restorations each having the shape indicated in FIG. 1 were manufactured as follows according to the first manufacturing method (building up method) described above.

Namely, first an abutment tooth model shown in FIG. 1 was manufactured in the usual way by using the composition which contains at least one oxide selected from the group comprising Zr, Y, and Ca. The composition of the abutment tooth model was shown in the attached Table 1. Moreover, the abutment tooth model was formed so as to be larger than the abutment tooth in the oral cavity to the extent of the degree of the inner part shrinkage of the green body taking the curing expansion and the thermal expansion into account.

Further, compositions for making metal materials constituting the respective prosthetic restorations were prepared. The substances used to form the compositions are indicated below. Moreover, each composition was kneaded for 60 minutes at 90° C. using a pressing kneader.

| | |
|---|---|
| Ti Powder (Average particle size 20 μm) | 92.5 wt % |
| In$_2$O$_3$ Powder (Average particle size 14 μm) | 0.5 wt % |
| Binder etc. | |
| Polystyrene | 2.5 wt % |
| Paraffin wax | 3.4 wt % |
| Dibutyl phthalate | 1.1 wt % |

The above-described compositions were then built up into the form of the prescribed prosthetic restoration on the abutment tooth model, respectively. In this case, each built up compound (green body) was formed so as to be larger than the intended shape to the extent of the degree of the shrinkage of the green body.

Next, the completed green bodies were subjected to a debinding treatment, respectively. The debinding treatment was carried out for 3 hours at from 400 to 500° C. under a reduced pressure of 1×10$^{-2}$ Torr.

Next, the green bodies which had been subjected to the debinding treatment were sintered as they are being attached to the respective abutment tooth model. The sintering was carried out for 3 hours at 1200° C. in an argon atmosphere.

Then, the respectively abutment tooth models were released (removed), thereby obtaining prosthetic restorations which were formed of metal sintered bodies each having the shape and structure shown in FIG. 1.

EXAMPLES 8 to 14

Prosthetic restorations each having the shape shown in FIG. 2 were manufactured according to the same manufacturing method used in Examples 1 to 7 except that the abutment tooth models were changed to the abutment tooth models shown in FIG. 2.

In these examples, each of the abutment tooth models included a surface layer, and each surface layer was formed by the method in which a liquid type composition obtained by solving a prescribed amount of $ZrO_2$, $Y_2O_3$ or CaO in alcohol was applied onto the respective abutment tooth model using a painting method, and it was then sintered at 900 to 1100° C.

The compositions of the respective parts of each abutment tooth model were as shown in the attached Table 2. In these examples, each of the abutment tooth models was formed with dimensions slightly larger than the abutment tooth in the oral cavity by taking the curing expansion upon molding and the thermal expansion upon sintering into account, in which they were formed so as to be larger to the extent of the degree of shrinkage of the respective green bodies by adjusting the thickness of the respective surface layers.

EXAMPLES 15 to 63

Prosthetic restorations each having the shape shown in FIG. 3 were manufactured according to the same manufacturing method used in Examples 1 to 7 except that the abutment tooth models were changed to the abutment tooth models shown in FIG. 3. In these prosthetic restorations, surface layers were formed in the same way as in Examples 8 to 14.

The compositions of the respective parts of the respective abutment tooth models were shown in the attached Tables 3 to 7. In these examples, each of the abutment tooth models was formed with dimensions slightly larger than the abutment tooth in the oral cavity by taking the curing expansion upon molding and the thermal expansion upon sintering into account, in which they were formed so as to be larger to the extent of the degree of shrinkage of the respective green bodies by adjusting the thickness of the respective surface layers.

EXAMPLES 64 to 70 and COMPARATIVE EXAMPLE 2

Prosthetic restoration having the shape shown in FIG. 1 was manufactured as follows according to the second manufacturing method (slip casting method) described above.

First, an inner mold was formed using a composition containing at least one oxide selected from the group comprising Zr, Y and Ca and then an outer mold was also formed using the same composition, to obtain a mold shown in FIG. 4. The composition of the mold was shown in the attached Table 8. In this case, the mold 8 was formed slightly larger than the intended shape to the extent of the degree of the shrinkage of the respective green bodies, tag the curing expansion upon molding and the thermal expansion upon sintering into account.

Further, a composition for making the metal material for the prosthetic restorations was prepared. The substances used to form the composition are indicated below. In this case, the composition was mixed at room temperature or less.

| | |
|---|---|
| Ti-2 wt % Al-1 wt % V Alloy Powder (Average particle size 18 $\mu$m) | 81.5 wt % |
| $CaSiO_3$ Powder (Average particle size $\mu$m) | 0.5 wt % |
| Dispersing medium etc. | |
| water | 17.5 wt % |
| polyvinyl alcohol | 0.5 wt % |

Next, thus obtained composition was injected into the respective cavity of the molds. Then, the dispersing medium in the respective compositions was absorbed by the respective molds to cure the compositions, thereby obtaining the green bodies.

Next, the completed green bodies were subjected to a debinding treatment. The debinding treatment was carried out for 3 hours at from 400 to 500° C. under a reduced pressure of $1\times10^{-2}$ Torr.

Next, the green bodies which had been subjected to the debinding treatment were sintered as they were being attached to the respective abutment tooth model. The sintering was carried out for 3 hours at 1200° C. in an argon atmosphere.

Then, the molds were removed, and the prosthetic restorations which were formed of the metal sintered body having the shape and structure shown in FIG. 1 were obtained.

EXAMPLES 71 to 77

Prosthetic restorations each having the shape shown in FIG. 5 were manufactured according to the same manufacturing method used in Examples 64 to 70 except that the abutment tooth models were changed to the abutment tooth models shown in FIG. 1.

In these examples, each of the inner and outer molds included a surface layer, and each surface layer was formed by the method in which a liquid type composition obtained by solving a prescribed amount of $ZrO_2$, $Y_2O_3$ or CaO in alcohol was applied onto the respective abutment tooth model using a dipping method, and it was then sintered at 900 to 1100° C.

The compositions of the respective parts of the respective molds were shown in the attached Table 9. In these examples, each of the molds was formed with dimensions slightly larger than the intended shape by taking the curing expansion upon molding and the thermal expansion upon sintering into account, in which they were formed so as to be larger to the extent of the degree of shrinkage of the respective green bodies by adjusting the thickness of the respective surface layers.

EXAMPLES 78 to 126

Prosthetic restorations each having the shape shown in FIG. 1 were manufactured according to the same manufacturing method used in Examples 64 to 70 except that the molds were changed to the molds shown in FIG. 6. In these examples, the formation of the surface layers for the inner and outer molds were performed in the same manner as in Examples 71 to 77.

The compositions of the respective parts of the respective molds were shown in the attached Table 10 to Table 14. In these examples, each of the molds was formed with dimensions slightly larger than the intended shape by taking the curing expansion upon molding and the thermal expansion upon sintering into account, in which they were formed so as to be larger to the extent of the degree of shrinkage of the respective green bodies by adjusting the thickness of the respective surface layers.

EXAMPLES 127 to 132

Prosthetic restorations each having the shape shown in FIG. 1 were manufactured according to the same manufacturing method used in Examples 64 to 126 except that the combination of the outer and inner molds of the respective molds were changed as shown in the attached Table 15.

The compositions of the respective parts of the respective molds were shown in the attached Table 15. In these examples, in the case where a surface layer was formed on the respective molds, each of the outer and inner molds of the respective moles was formed with dimensions slightly larger than the intended shape by taking the curing expansion upon molding and the thermal expansion upon sintering into account, in which they were formed so as to be larger to the extent of the degree of shrinkage of the respective green bodies by adjusting the thickness of the respective surface layers. On the other hand, in the case where no surface layer was formed, the respective molds were formed slightly larger than the intended shape to the extent of the degree of the shrinkage of the green body by taking the curing expansion upon molding and the thermal expansion upon sintering into account.

EXAMPLES 133 to 139 and COMPARATIVE EXAMPLE 3

Prosthetic restorations each having the shape shown in FIG. 1 were manufactured as follows according to the third manufacturing method (MIM) described above.

First, an inner mold was formed using a composition containing at least one oxide selected from the group comprising Zr, Y and Ca and then an outer mold was also formed using the same composition, to obtain a mold shown in FIG. 7. The composition of the mold was shown in the attached Table 16. In this case, the mold was formed slightly larger than the intended shape to the extent of the degree of the shrinkage of the respective green bodies, taking the curing expansion upon molding and the thermal expansion upon sintering into account.

Then, thus formed mold was mounted to the inside of the injection molding machine.

On the other hand, compositions constituting the metal materials for the prosthetic restorations were prepared. The substances used to form the compositions were indicated below. In this case, the compositions were kneaded for 60 minutes at 90° C. using a pressing kneader.

| | |
|---|---|
| Ti - 2 wt % Al - 1 wt % V Alloy Powder (Average particle size 18 μm) | 90 wt % |
| $Ca_3(PO_4)_2$ Powder (Average particle size 10 μm) | 1 wt % |
| Binder etc. | |
| Polystyrene | 2.7 wt % |
| Ethylene-vinyl acetate copolymer | 2.7 wt % |
| Paraffin wax | 2.3 wt % |
| Dibutyl phthalate | 1.3 wt % |

Next, the compositions were injected into the cavities of the respective molds to fill them with the compositions (injection molding was carried out), to obtain green bodies. The molding conditions at this time were as follows: the material temperature was 150° C.; the injection pressure was 100 $kgf/cm^2$; and the temperature at the mold was 20° C.

Next, the completed green bodies were subjected to a debinding treatment. The debinding treatment was carried out for 3 hours at from 400 to 500° C. under a reduced pressure of $1 \times 10^{-2}$ Torr.

Then, the green bodies which had been subjected to the debinding treatment were sintered as they were being attached to the respective molds. The sintering was carried out for 3 hours at 1200° C. in an argon atmosphere.

Then, the respective molds were removed, and prosthetic restorations which were composed of metal sintered bodies each having the shape shown in FIG. 1 were obtained.

EXAMPLES 140 to 146

Prosthetic restorations each having the shape shown in FIG. 1 were manufactured according to the same manufacturing method used in Examples 133 to 139 except that the molds were changed into those each having the structure shown in FIG. 8.

In these examples, each of the inner and outer molds included a surface layer, and each surface layer was formed by the method in which a liquid type composition obtained by solving a prescribed amount of $ZrO_2$, $Y_2O_3$ or CaO in alcohol was applied onto the respective molds using a dipping method, and it was then sintered at 900 to 1100° C. The compositions of the respective parts of the molds were shown in the attached Table 17. In this case, each of the molds was formed with dimensions slightly larger than the intended shape by taking the curing expansion upon molding and the thermal expansion upon sintering into account, in which they were formed so as to be larger to the extent of the degree of shrinkage of the respective green bodies by adjusting the thickness of the respective surface layers.

EXAMPLES 147 to 195

Prosthetic restorations each having the shape shown in FIG. 1 were manufactured according to the same manufacturing method used in Examples 133 to 139 except that the molds were changed into those each having the structure shown in FIG. 9.

The compositions of the respective parts of the molds were shown in the attached Table 18 to Table 22. In these examples, each of the molds was formed with dimensions slightly larger than the intended shape by taking the curing expansion upon molding and the thermal expansion upon sintering into account, in which they were formed so as to be larger to the extent of the degree of shrinkage of the respective green bodies by adjusting the thickness of the respective surface layers.

EXAMPLES 196 to 201

Prosthetic restorations each having the shape shown in FIG. 1 were manufactured according to the same manufacturing method used in Examples 133 to 195 except that the combination of the outer and inner molds of the respective molds were changed into those shown in the attached Table 23.

The compositions of the respective parts of the molds were shown in the attached Table 23. In these examples, in the case where a surface layer was formed on the respective molds, each of the outer and inner molds of the respective moles was formed with dimensions slightly larger than the intended shape by taking the curing expansion upon molding and the thermal expansion upon sintering into account, in which they were formed so as to be larger to the extent of the degree of shrinkage of the respective green bodies by adjusting the thickness of the respective surface layers. On the other hand, in the case where no surface layer was formed, the respective molds were formed slightly larger than the intended shape to the extent of the degree of the shrinkage of the green body by taking the curing expansion upon molding and the thermal expansion upon sintering into account.

Next, the mold release properties were evaluated for each of the prosthetic restorations in the Examples 1 to 201 and Comparative Examples 1 to 3. The results obtained were shown in the attached Table 24 to 33.

(Mold Release Property)

After firing the prosthetic restorations, the oxygen (O) content in the metal material of each of the prosthetic restorations were measured according to the infrared-absorbing analysis method. In the results of the measurement, higher oxygen content shows poor mold release property.

Further, after releasing (removing) the abutment tooth models or the molds (inner molds or outer molds) from the prosthetic restorations, the surfaces (surface conditions) of the prosthetic restorations were observed. In this case, evaluations were made using the symbol "X" where the reaction product at the sintering process was attached to the surface of the prosthetic restoration (stuck onto the surface thereof), the symbol "Δ" where a small amount of the reaction product was attached thereto, and the symbol "○" (where less reaction product was attached thereto.

(Consideration to the Results)

The results of the evaluations were shown in the attached Tables 24 to 33. As shown in these Tables, it was confirmed that all the prosthetic restorations in Examples 1–201 have an excellent mold release property and have no defect as well as their productions are very easy.

In particular, each of Examples 15 to 63, 78 to 126 and 147 to 195 has lower oxygen content in comparison with other Examples, so that it was understood that they have more excellent liability.

In contrast with these Examples, Comparative Examples 1 to 3 showed poor mold release property and confirmed that there is a defect that the reaction products produced when sintering were attached to the prosthetic restorations.

As described above, according to the abutment tooth model and the method of manufacturing a prosthetic restoration to be formed onto the abutment tooth model of the present invention, it is possible to prevent reaction from being caused between Ti or Ti alloy in the green body and the abutment tooth model or the mold during sintering process, thereby enabling to improve a mold release properly and to manufacture a high quality prosthetic restoration easily since no reaction product which is unnecessary by nature is attached thereto. Further, it is possible to provide a prosthetic restoration having excellent biocompatibility and bioaffinity, is light in weight, and has adequate mechanical strength and hardness.

Further, when a surface layer is formed on the abutment tooth model or the mold, the surface layer functions as a reaction preventing layer upon sintering. Further, it also functions as a spacer for compensating the shrinkage of the green body, so that it is not necessary to provide a spacer additionally, thus leading to easiness in manufacturing process.

Moreover, according to the present invention, when the prosthetic restoration is manufactured according to the powder metallurgy method such as the building up method, slip casting method and MIM and the like, the prosthetic restorations can be manufactured easily and in good yield even with complicated and intricate shapes. Further, the conditions such as composition and porosity and pore diameter of the metal material constituting the prosthetic restoration can be set easily and with a high degree of accuracy.

Finally, it should be noted that the present invention is not limited to the embodiments and examples described above, and the scope of the present invention will be determined only by the appended claims.

TABLE 1

(Building Up Method)

Composition of Abutment Tooth Model (wt %)

| | $CaSO_4 \cdot 2H_2O$ | $ZrO_2$ | $Y_2O_3$ | CaO |
|---|---|---|---|---|
| Example 1 | 20 | 80 | — | — |
| Example 2 | 30 | — | 70 | — |
| Example 3 | 50 | — | — | 50 |
| Example 4 | 15 | 40 | 45 | — |
| Example 5 | 25 | 60 | — | 15 |
| Example 6 | 10 | — | 55 | 35 |
| Example 7 | 15 | 35 | 30 | 20 |
| Comp. Ex. 1 | 100 | — | — | — |

TABLE 2

(Building Up Method)

| | Composition of Abutment Tooth Model (Inner Part) (wt %) | | | | Composition of Surface Layer (wt %) | | |
|---|---|---|---|---|---|---|---|
| | $CaSO_4 \cdot 2H_2O$ | $ZrO_2$ | $Y_2O_3$ | CaO | $ZrO_2$ | $Y_2O_3$ | CaO |
| Example 8 | 100 | — | — | — | 100 | — | — |
| Example 9 | 100 | — | — | — | — | 100 | — |
| Example 10 | 100 | — | — | — | — | — | 100 |
| Example 11 | 100 | — | — | — | 40 | 60 | — |
| Example 12 | 100 | — | — | — | — | 30 | 70 |
| Example 13 | 100 | — | — | — | 65 | — | 35 |
| Example 14 | 100 | — | — | — | 50 | 30 | 20 |

TABLE 3

(Building Up Method)

| | Composition of Abutment Tooth Model (Inner Part) (wt %) | | | | Composition of Surface Layer (wt %) | | |
|---|---|---|---|---|---|---|---|
| | $CaSO_4 \cdot 2H_2O$ | $ZrO_2$ | $Y_2O_3$ | CaO | $ZrO_2$ | $Y_2O_3$ | CaO |
| Example 15 | 20 | 80 | — | — | 100 | — | — |
| Example 16 | 20 | 80 | — | — | — | 100 | — |
| Example 17 | 20 | 80 | — | — | — | — | 100 |
| Example 18 | 20 | 80 | — | — | 40 | 60 | — |
| Example 19 | 20 | 80 | — | — | — | 30 | 70 |
| Example 20 | 20 | 80 | — | — | 65 | — | 35 |
| Example 21 | 20 | 80 | — | — | 50 | 30 | 20 |
| Example 22 | 30 | — | 70 | — | 100 | — | — |
| Example 23 | 30 | — | 70 | — | — | 100 | — |
| Example 24 | 30 | — | 70 | — | — | — | 100 |

Continued to Table 4

TABLE 4

(Building Up Method)

| | Composition of Abutment Tooth Model (Inner Part) (wt %) | | | | Composition of Surface Layer (wt %) | | |
|---|---|---|---|---|---|---|---|
| | $CaSO_4 \cdot 2H_2O$ | $ZrO_2$ | $Y_2O_3$ | CaO | $ZrO_2$ | $Y_2O_3$ | CaO |
| Example 25 | 30 | — | 70 | — | 40 | 60 | — |
| Example 26 | 30 | — | 70 | — | — | 30 | 70 |
| Example 27 | 30 | — | 70 | — | 65 | — | 35 |
| Example 28 | 30 | — | 70 | — | 50 | 30 | 20 |
| Example 29 | 50 | — | — | 50 | 100 | — | — |
| Example 30 | 50 | — | — | 50 | — | 100 | — |
| Example 31 | 50 | — | — | 50 | — | — | 100 |

TABLE 4-continued (Building Up Method)

| | Composition of Abutment Tooth Model (Inner Part) (wt %) | | | | Composition of Surface Layer (wt %) | | |
|---|---|---|---|---|---|---|---|
| | CaSO$_4$·2H$_2$O | ZrO$_2$ | Y$_2$O$_3$ | CaO | ZrO$_2$ | Y$_2$O$_3$ | CaO |
| Example 32 | 50 | — | — | 50 | 40 | 60 | — |
| Example 33 | 50 | — | — | 50 | — | 30 | 70 |
| Example 34 | 50 | — | — | 50 | 65 | — | 35 |

Continued to Table 5

TABLE 5

(Building Up Method)

| | Composition of Abutment Tooth Model (Inner Part) (wt %) | | | | Composition of Surface Layer (wt %) | | |
|---|---|---|---|---|---|---|---|
| | CaSO$_4$·2H$_2$O | ZrO$_2$ | Y$_2$O$_3$ | CaO | ZrO$_2$ | Y$_2$O$_3$ | CaO |
| Example 35 | 50 | — | — | 50 | 50 | 30 | 20 |
| Example 36 | 15 | 40 | 45 | — | 100 | — | — |
| Example 37 | 15 | 40 | 45 | — | — | 100 | — |
| Example 38 | 15 | 40 | 45 | — | — | — | 100 |
| Example 39 | 15 | 40 | 45 | — | 40 | 60 | — |
| Example 40 | 15 | 40 | 45 | — | — | 30 | 70 |
| Example 41 | 15 | 40 | 45 | — | 65 | — | 35 |
| Example 42 | 15 | 40 | 45 | — | 50 | 30 | 20 |
| Example 43 | 25 | 60 | — | 15 | 100 | — | — |
| Example 44 | 25 | 60 | — | 15 | — | 100 | — |

Continued to Table 6

TABLE 6

(Building Up Method)

| | Composition of Abutment Tooth Model (Inner Part) (wt %) | | | | Composition of Surface Layer (wt %) | | |
|---|---|---|---|---|---|---|---|
| | CaSO$_4$·2H$_2$O | ZrO$_2$ | Y$_2$O$_3$ | CaO | ZrO$_2$ | Y$_2$O$_3$ | CaO |
| Example 45 | 25 | 60 | — | 15 | — | — | 100 |
| Example 46 | 25 | 60 | — | 15 | 40 | 60 | — |
| Example 47 | 25 | 60 | — | 15 | — | 30 | 70 |
| Example 48 | 25 | 60 | — | 15 | 65 | — | 35 |
| Example 49 | 25 | 60 | — | 15 | 50 | 30 | 20 |
| Example 50 | 10 | — | 55 | 35 | 100 | — | — |
| Example 51 | 10 | — | 55 | 35 | — | 100 | — |
| Example 52 | 10 | — | 55 | 35 | — | — | 100 |
| Example 53 | 10 | — | 55 | 35 | 40 | 60 | — |
| Example 54 | 10 | — | 55 | 35 | — | 30 | 70 |

Continued to Table 7

TABLE 7

(Building Up Method)

| | Composition of Abutment Tooth Model (Inner Part) (wt %) | | | | Composition of Surface Layer (wt %) | | |
|---|---|---|---|---|---|---|---|
| | CaSO$_4$·2H$_2$O | ZrO$_2$ | Y$_2$O$_3$ | CaO | ZrO$_2$ | Y$_2$O$_3$ | CaO |
| Example 55 | 10 | — | 55 | 35 | 65 | — | 35 |
| Example 56 | 10 | — | 55 | 35 | 50 | 30 | 20 |
| Example 57 | 15 | 35 | 30 | 20 | 100 | — | — |

TABLE 7-continued (Building Up Method)

| | Composition of Abutment Tooth Model (Inner Part) (wt %) | | | | Composition of Surface Layer (wt %) | | |
|---|---|---|---|---|---|---|---|
| | CaSO$_4$·2H$_2$O | ZrO$_2$ | Y$_2$O$_3$ | CaO | ZrO$_2$ | Y$_2$O$_3$ | CaO |
| Example 58 | 15 | 35 | 30 | 20 | — | 100 | — |
| Example 59 | 15 | 35 | 30 | 20 | — | — | 100 |
| Example 60 | 15 | 35 | 30 | 20 | 40 | 60 | — |
| Example 61 | 15 | 35 | 30 | 20 | — | 30 | 70 |
| Example 62 | 15 | 35 | 30 | 20 | 65 | — | 35 |
| Example 63 | 15 | 35 | 30 | 20 | 50 | 30 | 20 |

TABLE 8

(Slip Casting Method)

| | Composition of Mold (Inner Mold and Outer Mold) (wt %) | | | |
|---|---|---|---|---|
| | CaSO$_4$·2H$_2$O | ZrO$_2$ | Y$_2$O$_3$ | CaO |
| Example 64 | 20 | 80 | — | — |
| Example 65 | 30 | — | 70 | — |
| Example 66 | 50 | — | — | 50 |
| Example 67 | 15 | 40 | 45 | — |
| Example 68 | 25 | 60 | — | 15 |
| Example 69 | 10 | — | 55 | 35 |
| Example 70 | 15 | 35 | 30 | 20 |
| Comp. Ex. 2 | 100 | — | — | — |

TABLE 9

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$·2H$_2$O | ZrO$_2$ | Y$_2$O$_3$ | CaO | ZrO$_2$ | Y$_2$O$_3$ | CaO |
| Example 71 | 100 | — | — | — | 100 | — | — |
| Example 72 | 100 | — | — | — | — | 100 | — |
| Example 73 | 100 | — | — | — | — | — | 100 |
| Example 74 | 100 | — | — | — | 40 | 60 | — |
| Example 75 | 100 | — | — | — | — | 30 | 70 |
| Example 76 | 100 | — | — | — | 65 | — | 35 |
| Example 77 | 100 | — | — | — | 50 | 30 | 20 |

TABLE 10

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$·2H$_2$O | ZrO$_2$ | Y$_2$O$_3$ | CaO | ZrO$_2$ | Y$_2$O$_3$ | CaO |
| Example 78 | 20 | 80 | — | — | 100 | — | — |
| Example 79 | 20 | 80 | — | — | — | 100 | — |
| Example 80 | 20 | 80 | — | — | — | — | 100 |
| Example 81 | 20 | 80 | — | — | 40 | 60 | — |
| Example 82 | 20 | 80 | — | — | — | 30 | 70 |
| Example 83 | 20 | 80 | — | — | 65 | — | 35 |

TABLE 10-continued (Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 84 | 20 | 80 | — | — | 50 | 30 | 20 |
| Example 85 | 30 | — | 70 | — | 100 | — | — |
| Example 86 | 30 | — | 70 | — | — | 100 | — |
| Example 87 | 30 | — | 70 | — | — | — | 100 |

Continued to Table 11

TABLE 11

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 88 | 30 | — | 70 | — | 40 | 60 | — |
| Example 89 | 30 | — | 70 | — | — | 30 | 70 |
| Example 90 | 30 | — | 70 | — | 65 | — | 35 |
| Example 91 | 30 | — | 70 | — | 50 | 30 | 20 |
| Example 92 | 50 | — | — | 50 | 100 | — | — |
| Example 93 | 50 | — | — | 50 | — | 100 | — |
| Example 94 | 50 | — | — | 50 | — | — | 100 |
| Example 95 | 50 | — | — | 50 | 40 | 60 | — |
| Example 96 | 50 | — | — | 50 | — | 30 | 70 |
| Example 97 | 50 | — | — | 50 | 65 | — | 35 |

Continued to Table 12

TABLE 12

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 98 | 50 | — | — | 50 | 50 | 30 | 20 |
| Example 99 | 15 | 40 | 45 | — | 100 | — | — |
| Example 100 | 15 | 40 | 45 | — | — | 100 | — |
| Example 101 | 15 | 40 | 45 | — | — | 100 | — |
| Example 102 | 15 | 40 | 45 | — | 40 | 60 | — |
| Example 103 | 15 | 40 | 45 | — | — | 30 | 70 |
| Example 104 | 15 | 40 | 45 | — | 65 | — | 35 |
| Example 105 | 15 | 40 | 45 | — | 50 | 30 | 20 |
| Example 106 | 25 | 60 | — | 15 | 100 | — | — |
| Example 107 | 25 | 60 | — | 15 | — | 100 | — |

Continued to Table 13

TABLE 13

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 108 | 25 | 60 | — | 15 | — | — | 100 |
| Example 109 | 25 | 60 | — | is | 40 | 60 | — |
| Example 110 | 25 | 60 | — | 15 | — | 30 | 70 |
| Example 111 | 25 | 60 | — | 15 | 65 | — | 35 |
| Example 112 | 25 | 60 | — | 15 | 50 | 30 | 20 |
| Example 113 | 10 | — | 55 | 35 | 100 | — | — |
| Example 114 | 10 | — | 55 | 35 | — | 100 | — |
| Example 115 | 10 | — | 55 | 35 | — | — | 100 |
| Example 116 | 10 | — | 55 | 35 | 40 | 60 | — |
| Example 117 | 10 | — | 55 | 35 | — | 30 | 70 |

Continued to Table 14

TABLE 14

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 118 | 10 | — | 55 | 35 | 65 | — | 35 |
| Example 119 | 10 | — | 55 | 35 | 50 | 30 | 20 |
| Example 120 | 15 | 35 | 30 | 20 | 100 | — | — |
| Example 121 | 15 | 35 | 30 | 20 | — | 100 | — |
| Example 122 | 15 | 35 | 30 | 20 | — | — | 100 |
| Example 123 | 15 | 35 | 30 | 20 | 40 | 60 | — |
| Example 124 | 15 | 35 | 30 | 20 | — | 30 | 70 |
| Example 125 | 15 | 35 | 30 | 20 | 65 | — | 35 |
| Example 126 | 15 | 35 | 30 | 20 | 50 | 30 | 20 |

TABLE 15

(Slip Casting Method)

| | | Composition of Mold (Inner Part) (wt %) | | | | Composition of Surface Layer (wt %) | | |
|---|---|---|---|---|---|---|---|---|
| | | CaSO$_4$.2H$_2$O | ZrO$_2$ | Y$_2$O$_3$ | CaO | ZrO$_2$ | Y$_2$O$_3$ | CaO |
| Example 127 | Outer Mold | 15 | 35 | 30 | 20 | (No Surface Layer) | | |
| | Inner Mold | 100 | — | — | — | 50 | 30 | 20 |

TABLE 15-continued (Slip Casting Method)

| | | Composition of Mold (Inner Part) (wt %) | | | | Composition of Surface Layer (wt %) | | |
|---|---|---|---|---|---|---|---|---|
| | | CaSO$_4$.2H$_2$O | ZrO$_2$ | Y$_2$O$_3$ | CaO | ZrO$_2$ | Y$_2$O$_3$ | CaO |
| Example 128 | Outer Mold | 15 | 35 | 30 | 20 | (No Surface Layer) | | |
| | Inner Mold | 15 | 35 | 30 | 20 | 50 | 30 | 20 |
| Example 129 | Outer Mold | 100 | — | — | — | 50 | 30 | 20 |
| | Inner Mold | 15 | 35 | 30 | 20 | (No Surface Layer) | | |
| Example 130 | Outer Mold | 100 | — | — | — | 50 | 30 | 20 |
| | Inner Mold | 15 | 35 | 30 | 20 | 50 | 30 | 20 |
| Example 131 | Outer Mold | 15 | 35 | 30 | 20 | 50 | 30 | 20 |
| | Inner Mold | 15 | 35 | 30 | 20 | (No Surface Layer) | | |
| Example 132 | Outer Mold | 15 | 35 | 30 | 20 | 50 | 30 | 20 |
| | Inner Mold | 100 | — | — | — | 50 | 30 | 20 |

TABLE 16

(MIM)

Composition of Mold (Inner Mold and Outer Mold) (wt %)

| | CaSO$_4$ · 2H$_2$O | ZrO$_2$ | Y$_2$O$_3$ | CaO |
|---|---|---|---|---|
| Example 133 | 20 | 80 | — | — |
| Example 134 | 30 | — | 70 | — |
| Example 135 | 50 | — | — | 50 |
| Example 136 | 15 | 40 | 45 | — |
| Example 137 | 25 | 60 | — | 15 |
| Example 138 | 10 | — | 55 | 35 |
| Example 139 | 15 | 35 | 30 | 20 |
| Comp. Ex. 3 | 100 | — | — | — |

TABLE 17

(MIM)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 140 | 100 | — | — | — | 100 | — | — |
| Example 141 | 100 | — | — | — | — | 100 | — |
| Example 142 | 100 | — | — | — | — | — | 100 |
| Example 143 | 100 | — | — | — | 40 | 60 | — |
| Example 144 | 100 | — | — | — | — | 30 | 70 |
| Example 145 | 100 | — | — | — | 65 | — | 35 |
| Example 146 | 100 | — | — | — | 50 | 30 | 20 |

TABLE 18

(MIM)

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 147 | 20 | 80 | — | — | 100 | — | — |
| Example 148 | 20 | 80 | — | — | — | 100 | — |
| Example 149 | 20 | 80 | — | — | — | — | 100 |
| Example 150 | 20 | 80 | — | — | 40 | 60 | — |
| Example 151 | 20 | 80 | — | — | — | 30 | 70 |
| Example 152 | 20 | 80 | — | — | 65 | — | 35 |
| Example 153 | 20 | 80 | — | — | 50 | 30 | 20 |
| Exanple 154 | 30 | — | 70 | — | 100 | — | — |
| Example 155 | 30 | — | 70 | — | — | 100 | — |
| Example 156 | 30 | — | 70 | — | — | — | 100 |

Continued to Table 19

TABLE 19

(MIM)

(Slip Casting Method)

| | Composition of Mold (Inner Part of Inner Mold and Outer Mold) (wt %) | | | | Composition of Surface Layer (wt %) | | |
|---|---|---|---|---|---|---|---|
| | CaSO$_4$.2H$_2$O | ZrO$_2$ | Y$_2$O$_3$ | CaO | ZrO$_2$ | Y$_2$O$_3$ | CaO |
| Example 157 | 30 | — | 70 | — | 40 | 60 | — |
| Example 158 | 30 | — | 70 | — | — | 30 | 70 |
| Example 159 | 30 | — | 70 | — | 65 | — | 35 |
| Example 160 | 30 | — | 70 | — | 50 | 30 | 20 |
| Example 161 | 50 | — | — | 50 | 100 | — | — |
| Example 162 | 50 | — | — | 50 | — | 100 | — |
| Example 163 | 50 | — | — | 50 | — | — | 100 |
| Example 164 | 50 | — | — | 50 | 40 | 60 | — |
| Example 165 | 50 | — | — | 50 | — | 30 | 70 |
| Example 166 | 50 | — | — | 50 | 65 | — | 35 |

Continued to Table 20

TABLE 20

(MIM)

| | Composition of Mold (Inner Part of Inner Mold and Outer Mold) (wt %) | | | | Composition of Surface Layer (wt %) | | |
|---|---|---|---|---|---|---|---|
| | $CaSO_4 \cdot 2H_2O$ | $ZrO_2$ | $Y_2O_3$ | CaO | $ZrO_2$ | $Y_2O_3$ | CaO |
| Example 167 | 50 | — | — | 50 | 50 | 30 | 20 |
| Example 168 | 15 | 40 | 45 | — | 100 | — | — |
| Example 169 | 15 | 40 | 45 | — | — | 100 | — |
| Example 170 | 15 | 40 | 45 | — | — | — | 100 |
| Example 171 | 15 | 40 | 45 | — | 40 | 60 | — |
| Example 172 | 15 | 40 | 45 | — | — | 30 | 70 |
| Example 173 | 15 | 40 | 45 | — | 65 | — | 35 |
| Example 174 | 15 | 40 | 45 | — | 50 | 30 | 20 |
| Example 175 | 25 | 60 | — | 15 | 100 | — | — |
| Example 176 | 25 | 60 | — | 15 | — | 100 | — |

Continued to Table 21

TABLE 21

(MIM)

| | Composition of Mold (Inner Part of Inner Mold and Outer Mold) (wt %) | | | | Composition of Surface Layer (wt %) | | |
|---|---|---|---|---|---|---|---|
| | $CaSO_4 \cdot 2H_2O$ | $ZrO_2$ | $Y_2O_3$ | CaO | $ZrO_2$ | $Y_2O_3$ | CaO |
| Example 177 | 25 | 60 | — | 15 | — | — | 100 |
| Example 178 | 25 | 60 | — | 15 | 40 | 60 | — |
| Example 179 | 25 | 60 | — | 15 | — | 30 | 70 |
| Example 180 | 25 | 60 | — | 15 | 65 | — | 35 |
| Example 181 | 25 | 60 | — | 15 | 50 | 30 | 20 |
| Example 182 | 10 | — | 55 | 35 | 100 | — | — |
| Example 183 | 10 | — | 55 | 35 | — | 100 | — |
| Example 184 | 10 | — | 55 | 35 | — | — | 100 |
| Example 185 | 10 | — | 55 | 35 | 40 | 60 | — |
| Example 186 | 10 | — | 55 | 35 | — | 30 | 70 |

Continued to Table 22

TABLE 22

(MIM)

| | Composition of Mold (Inner Part of Inner Mold and Outer Mold) (wt %) | | | | Composition of Surface Layer (wt %) | | |
|---|---|---|---|---|---|---|---|
| | $CaSO_4 \cdot 2H_2O$ | $ZrO_2$ | $Y_2O_3$ | CaO | $ZrO_2$ | $Y_2O_3$ | CaO |
| Example 187 | 10 | — | 55 | 35 | 65 | — | 35 |
| Example 188 | 10 | — | 55 | 35 | 50 | 30 | 20 |
| Example 189 | 15 | 35 | 30 | 20 | 100 | — | — |
| Example 190 | 15 | 35 | 30 | 20 | — | 100 | — |
| Example 191 | 15 | 35 | 30 | 20 | — | — | 100 |
| Example 192 | 15 | 35 | 30 | 20 | 40 | 60 | — |
| Example 193 | 15 | 35 | 30 | 20 | — | 30 | 70 |
| Example 194 | 15 | 35 | 30 | 20 | 65 | — | 35 |
| Example 195 | 15 | 35 | 30 | 20 | 50 | 30 | 20 |

TABLE 23

(MIM)

| | | Composition of Mold (Inner Part) (wt %) | | | | Composition of Surface Layer (wt %) | | |
|---|---|---|---|---|---|---|---|---|
| | | $CaSO_4 \cdot 2H_2O$ | $ZrO_2$ | $Y_2O_3$ | CaO | $ZrO_2$ | $Y_2O_3$ | CaO |
| Example 196 | Outer Mold | 15 | 35 | 30 | 20 | (No Surface Layer) | | |
| | Inner Mold | 100 | — | — | — | 50 | 30 | 20 |
| Example 197 | Outer Mold | 15 | 35 | 30 | 20 | (No Surface Layer) | | |
| | Inner Mold | 15 | 35 | 30 | 20 | 50 | 30 | 20 |
| Example 198 | Outer Mold | 100 | — | — | — | 50 | 30 | 20 |
| | Inner Mold | 15 | 35 | 30 | 20 | (No Surface Layer) | | |
| Example 199 | Outer Mold | 100 | — | — | — | 50 | 30 | 20 |
| | Inner Mold | 15 | 35 | 30 | 20 | 50 | 30 | 20 |
| Example 200 | Outer Mold | 15 | 35 | 30 | 20 | 50 | 30 | 20 |
| | Inner Mold | 15 | 35 | 30 | 20 | (No Surface Layer) | | |
| Example 201 | Outer Mold | 15 | 35 | 30 | 20 | 50 | 30 | 20 |
| | Inner Mold | 100 | — | — | — | 50 | 30 | 20 |

TABLE 24

| | Mold Release Property | |
|---|---|---|
| | Ratio of Oxygen Content (wt %) | Surface Condition |
| Example 1 | 0.45 | ◯ |
| Example 2 | 0.48 | ◯ |
| Example 3 | 0.65 | ◯ |

TABLE 24-continued

Mold Release Property

| | Ratio of Oxygen Content (wt %) | Surface Condition |
|---|---|---|

TABLE 24-continued

Mold Release Property

| | Ratio of Oxygen Content (wt %) | Surface Condition |
|---|---|---|
| Example 4 | 0.43 | ○ |
| Example 5 | 0.49 | ○ |
| Example 6 | 0.45 | ○ |
| Example 7 | 0.47 | ○ |
| Comp. Ex. 1 | 2.20 | × |
| Example 8 | 0.37 | ○ |
| Example 9 | 0.38 | ○ |
| Example 10 | 0.40 | ○ |
| Example 11 | 0.38 | ○ |
| Example 12 | 0.40 | ○ |
| Example 13 | 0.39 | ○ |
| Example 14 | 0.39 | ○ |
| Example 15 | 0.31 | ○ |
| Example 16 | 0.31 | ○ |
| Example 17 | 0.33 | ○ |
| Example 18 | 0.30 | ○ |
| Example 19 | 0.32 | ○ |

Continued to Table 25

TABLE 25

Mold Release Property

| | Ratio of Oxygen Content (wt %) | Surface Condition |
|---|---|---|
| Example 20 | 0.32 | ○ |
| Example 21 | 0.31 | ○ |
| Example 22 | 0.31 | ○ |
| Example 23 | 0.30 | ○ |
| Example 24 | 0.33 | ○ |
| Example 25 | 0.31 | ○ |
| Example 26 | 0.32 | ○ |
| Example 27 | 0.31 | ○ |
| Example 28 | 0.31 | ○ |
| Example 29 | 0.32 | ○ |
| Example 30 | 0.31 | ○ |
| Example 31 | 0.34 | ○ |
| Example 32 | 0.31 | ○ |
| Example 33 | 0.33 | ○ |
| Example 34 | 0.33 | ○ |
| Example 35 | 0.32 | ○ |
| Example 36 | 0.30 | ○ |
| Example 37 | 0.30 | ○ |
| Example 38 | 0.31 | ○ |
| Example 39 | 0.30 | ○ |

Continued to Table 26

TABLE 26

Mold Release Property

| | Ratio of Oxygen Content (wt %) | Surface Condition |
|---|---|---|
| Example 40 | 0.31 | ○ |
| Example 41 | 0.31 | ○ |
| Example 42 | 0.31 | ○ |
| Example 43 | 0.31 | ○ |
| Example 44 | 0.31 | ○ |
| Example 45 | 0.32 | ○ |

TABLE 26-continued

Mold Release Property

| | Ratio of Oxygen Content (wt %) | Surface Condition |
|---|---|---|
| Example 46 | 0.31 | ○ |
| Example 47 | 0.32 | ○ |
| Example 48 | 0.32 | ○ |
| Example 49 | 0.32 | ○ |
| Example 50 | 0.32 | ○ |
| Example 51 | 0.32 | ○ |
| Example 52 | 0.32 | ○ |
| Example 53 | 0.31 | ○ |
| Example 54 | 0.32 | ○ |
| Example 55 | 0.32 | ○ |
| Example 56 | 0.31 | ○ |
| Example 57 | 0.30 | ○ |
| Example 58 | 0.30 | ○ |
| Example 59 | 0.31 | ○ |

Continued to Table 27

TABLE 27

Mold Release Property

| | Ratio of Oxygen Content (wt %) | Surface Condition |
|---|---|---|
| Example 60 | 0.30 | ○ |
| Example 61 | 0.31 | ○ |
| Example 62 | 0.30 | ○ |
| Example 63 | 0.30 | ○ |
| Example 64 | 0.46 | ○ |
| Example 65 | 0.49 | ○ |
| Example 66 | 0.60 | ○ |
| Example 67 | 0.45 | ○ |
| Example 68 | 0.48 | ○ |
| Example 69 | 0.45 | ○ |
| Example 70 | 0.46 | ○ |
| Comp. Ex. 2 | 2.52 | × |
| Example 71 | 0.40 | ○ |
| Example 72 | 0.41 | ○ |
| Example 73 | 0.43 | ○ |
| Example 74 | 0.42 | ○ |
| Example 75 | 0.42 | ○ |
| Example 76 | 0.41 | ○ |
| Example 77 | 0.41 | ○ |
| Example 78 | 0.33 | ○ |

Continued to Table 28

TABLE 28

Mold Release Property

| | Ratio of Oxygen Content (wt %) | Surface Condition |
|---|---|---|
| Example 79 | 0.32 | ○ |
| Example 80 | 0.34 | ○ |
| Example 81 | 0.34 | ○ |
| Example 82 | 0.32 | ○ |
| Example 83 | 0.33 | ○ |
| Example 84 | 0.32 | ○ |
| Example 85 | 0.32 | ○ |
| Example 86 | 0.32 | ○ |
| Example 87 | 0.34 | ○ |
| Example 88 | 0.33 | ○ |
| Example 89 | 0.33 | ○ |
| Example 90 | 0.32 | ○ |
| Example 91 | 0.32 | ○ |
| Example 92 | 0.33 | ○ |
| Example 93 | 0.33 | ○ |
| Example 94 | 0.35 | ○ |
| Example 95 | 0.32 | ○ |

TABLE 28-continued

| | Mold Release Property | |
|---|---|---|
| | Ratio of Oxygen Content (wt %) | Surface Condition |
| Example 96 | 0.33 | ○ |
| Example 97 | 0.33 | ○ |
| Example 98 | 0.33 | ○ |

Continued to Table 29

TABLE 29

| | Mold Release Property | |
|---|---|---|
| | Ratio of Oxygen Content (wt %) | Surface Condition |
| Example 99 | 0.31 | ○ |
| Example 100 | 0.30 | ○ |
| Example 101 | 0.31 | ○ |
| Example 102 | 0.30 | ○ |
| Example 103 | 0.31 | ○ |
| Example 104 | 0.31 | ○ |
| Example 105 | 0.30 | ○ |
| Example 106 | 0.32 | ○ |
| Example 107 | 0.32 | ○ |
| Example 108 | 0.33 | ○ |
| Example 109 | 0.32 | ○ |
| Example 110 | 0.33 | ○ |
| Example 111 | 0.33 | ○ |
| Example 112 | 0.32 | ○ |
| Example 113 | 0.32 | ○ |
| Example 114 | 0.31 | ○ |
| Example 115 | 0.32 | ○ |
| Example 116 | 0.32 | ○ |
| Example 117 | 0.32 | ○ |
| Example 118 | 0.32 | ○ |

Continued to Table 30

TABLE 30

| | Mold Release Property | |
|---|---|---|
| | Ratio of Oxygen Content (wt %) | Surface Condition |
| Example 119 | 0.31 | ○ |
| Example 120 | 0.32 | ○ |
| Example 121 | 0.32 | ○ |
| Example 122 | 0.33 | ○ |
| Example 123 | 0.32 | ○ |
| Example 124 | 0.33 | ○ |
| Example 125 | 0.32 | ○ |
| Example 126 | 0.32 | ○ |
| Example 127 | 0.44 | ○ |
| Example 128 | 0.42 | ○ |
| Example 129 | 0.44 | ○ |
| Example 130 | 0.37 | ○ |
| Example 131 | 0.43 | ○ |
| Example 132 | 0.36 | ○ |
| Example 133 | 0.44 | ○ |
| Example 134 | 0.48 | ○ |
| Example 135 | 0.58 | ○ |
| Example 136 | 0.41 | ○ |
| Example 137 | 0.43 | ○ |
| Example 138 | 0.43 | ○ |

Continued to Table 31

TABLE 31

| | Mold Release Property | |
|---|---|---|
| | Ratio of Oxygen Content (wt %) | Surface Condition |
| Example 139 | 0.42 | ○ |
| Comp. Ex. 3 | 2.15 | × |
| Example 140 | 0.35 | ○ |
| Example 141 | 0.36 | ○ |
| Example 142 | 0.38 | ○ |
| Example 143 | 0.35 | ○ |
| Example 144 | 0.38 | ○ |
| Example 145 | 0.37 | ○ |
| Example 146 | 0.37 | ○ |
| Example 147 | 0.30 | ○ |
| Example 148 | 0.30 | ○ |
| Example 149 | 0.31 | ○ |
| Example 150 | 0.30 | ○ |
| Example 151 | 0.31 | ○ |
| Example 152 | 0.30 | ○ |
| Example 153 | 0.30 | ○ |
| Example 154 | 0.30 | ○ |
| Example 155 | 0.31 | ○ |
| Example 156 | 0.31 | ○ |
| Example 157 | 0.31 | ○ |

Continued to Table 32

TABLE 32

| | Mold Release Property | |
|---|---|---|
| | Ratio of Oxygen Content (wt %) | Surface Condition |
| Example 158 | 0.31 | ○ |
| Example 159 | 0.31 | ○ |
| Example 160 | 0.31 | ○ |
| Example 161 | 0.33 | ○ |
| Example 162 | 0.32 | ○ |
| Example 163 | 0.34 | ○ |
| Example 164 | 0.32 | ○ |
| Example 165 | 0.33 | ○ |
| Example 166 | 0.33 | ○ |
| Example 167 | 0.32 | ○ |
| Example 168 | 0.29 | ○ |
| Example 169 | 0.29 | ○ |
| Example 170 | 0.30 | ○ |
| Example 171 | 0.29 | ○ |
| Example 172 | 0.30 | ○ |
| Example 173 | 0.30 | ○ |
| Example 174 | 0.29 | ○ |
| Example 175 | 0.30 | ○ |
| Example 176 | 0.30 | ○ |
| Example 177 | 0.32 | ○ |
| Example 178 | 0.31 | ○ |
| Example 179 | 0.32 | ○ |

Continued to Table 33

TABLE 33

| | Mold Release Property | |
|---|---|---|
| | Ratio of Oxygen Content (wt %) | Surface Condition |
| Example 180 | 0.31 | ○ |
| Example 181 | 0.31 | ○ |
| Example 182 | 0.31 | ○ |
| Example 183 | 0.31 | ○ |
| Example 184 | 0.33 | ○ |
| Example 185 | 0.32 | ○ |
| Example 186 | 0.32 | ○ |
| Example 187 | 0.31 | ○ |
| Example 188 | 0.31 | ○ |

TABLE 33-continued

| | Mold Release Property | |
|---|---|---|
| | Ratio of Oxygen Content (wt %) | Surface Condition |
| Example 189 | 0.30 | ○ |
| Example 190 | 0.31 | ○ |
| Example 191 | 0.31 | ○ |
| Example 192 | 0.30 | ○ |
| Example 193 | 0.31 | ○ |
| Example 194 | 0.30 | ○ |
| Example 195 | 0.30 | ○ |
| Example 196 | 0.41 | ○ |
| Example 197 | 0.37 | ○ |
| Example 198 | 0.41 | ○ |
| Example 199 | 0.34 | ○ |
| Example 200 | 0.36 | ○ |
| Example 201 | 0.34 | ○ |

What is claimed is:

1. A method of manufacturing a prosthetic restoration, comprising the steps of:

preparing an abutment tooth model:

building up a green body for a prosthetic restoration which is to be attached to an abutment tooth onto said abutment tooth model, in which the green body being formed of a composition containing Ti powder or Ti alloy powder as its main component, sintering the green body together with the abutment tooth model to manufacture the prosthetic restoration from the sintered body, wherein said abutment tooth model having a portion to be in contact with said green body, and at least said portion of the abutment tooth model being formed of a material containing at least one oxide selected from the group comprising Zr, Y and Ca;

wherein said abutment tooth model includes a surface layer which constitutes said portion of said abutment tooth model, and said surface layer is formed of a material containing at least one oxide selected from the group comprising Zr, Y and Ca as its main component; and wherein said surface layer has a thickness corresponding to a shrinkage that is caused when the green body is sintered.

2. A method of manufacturing a prosthetic restoration, comprising the steps of:

preparing an inner mold and an outer mold for defining a cavity between said inner and outer molds:

injecting a composition containing Ti powder or Ti alloy powder as its main component into said cavity to obtain a green body for a prosthetic restoration, and sintering the green body together with the inner and outer molds to manufacture the prosthetic restoration from the sintered body;

wherein said inner and/or outer molds include a portion to be in contact with the green body, and at least the portion of said molds is formed of a material containing at least one oxide selected from the group comprising Zr, Y and Ca, wherein at least the portion of said inner and/or outer molds which is to be in contact with the green body includes a surface layer, and said surface layer is formed of a material containing at least one oxide selected from the group comprising Zr, Y and Ca as its main component; and wherein said surface layer has a thickness corresponding to a shrinkage that would occur when the green body is sintered.

3. A method of manufacturing a prosthetic restoration, comprising the steps of:

preparing an inner mold and an outer mold for defining a cavity between said inner and outer molds:

injecting a composition containing Ti powder or Ti alloy powder as its main component into said cavity to obtain a green body for a prosthetic restoration; and sintering the green body together with the inner and outer molds to manufacture the prosthetic restoration from the sintered body;

wherein said inner and/or outer molds include a portion to be in contact with the green body, and at least the portion of said molds is formed of a material containing at least one oxide selected from the group comprising Zr, Y and Ca;

wherein both the inner and/or outer molds include a portion to be in contact with the green body, and at least the portion of said molds is formed of a material containing at least one oxide selected from the group comprising Zr, Y and Ca;

wherein both the inner and/or outer molds are formed of a material containing at least one oxide selected from the group comprising Zr, Y and Ca;

wherein at least the portion of said inner and/or outer molds which is to be in contact with the green body includes a surface layer, and said surface layer is formed of a material containing at least one oxide selected from the group comprising Zr, Y and Ca as its main component; and wherein said surface layer has a thickness corresponding to a shrinkage that would occur when the green body is sintered.

* * * * *